(12) United States Patent
Wechter et al.

(10) Patent No.: US 10,456,586 B2
(45) Date of Patent: Oct. 29, 2019

(54) USER INTERFACE FOR NEUROSTIMULATION WAVEFORM COMPOSITION

(71) Applicant: Boston Scientific Neuromodulation Corporation, Valencia, CA (US)

(72) Inventors: David Ernest Wechter, San Francisco, CA (US); David Lubensky, San Francisco, CA (US); Brian Hoffer, San Francisco, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 231 days.

(21) Appl. No.: 15/290,776

(22) Filed: Oct. 11, 2016

(65) Prior Publication Data

US 2017/0106197 A1   Apr. 20, 2017

Related U.S. Application Data

(60) Provisional application No. 62/333,551, filed on May 9, 2016, provisional application No. 62/241,965, filed on Oct. 15, 2015.

(51) Int. Cl.
*A61N 1/36* (2006.01)
*A61N 1/372* (2006.01)
(Continued)

(52) U.S. Cl.
CPC .......... *A61N 1/37252* (2013.01); *A61N 1/36* (2013.01); *A61N 1/3605* (2013.01);
(Continued)

(58) Field of Classification Search
CPC .... A61N 1/36; A61N 1/36017; A61N 1/3605; A61N 1/36146; A61N 1/3787;
(Continued)

(56) References Cited

U.S. PATENT DOCUMENTS 4,255,790 A   3/1981   Hondeghem
4,931,858 A   6/1990   Honjo et al.
(Continued)

FOREIGN PATENT DOCUMENTS

AU   2015318142 B2   6/2018
AU   2015343483 B2   6/2018
(Continued)

OTHER PUBLICATIONS

"U.S. Appl. No. 14/853,589, Non Final Office Action dated Aug. 17, 2016", 14 pgs.
(Continued)

*Primary Examiner* — Jon Eric C Morales
(74) *Attorney, Agent, or Firm* — Schwegman Lundberg & Woessner, P.A.

(57) ABSTRACT

An example of a system for programming a neurostimulator may include a storage device and a user interface. The storage device may be configured to store waveform building blocks. The user interface may include a display screen, a user input device, and an interface control circuit. The interface control circuit may include a waveform composer configured to allow for composition of one of more building blocks and composition of a pattern of neurostimulation pulses using selected one or more waveform building blocks. The waveform composer may include a library controller and waveform building block editors. The library controller may be configured to display a library management area on the screen. The displayed library management area allows a user to manage the stored waveform building blocks. The waveform building block editors may each be configured to allow the user to compose a type of the waveform building blocks.

20 Claims, 32 Drawing Sheets

(51) Int. Cl.
  *G06F 19/00* (2018.01)
  *G16H 40/63* (2018.01)
  *G16H 50/30* (2018.01)
  *G16H 20/70* (2018.01)

(52) U.S. Cl.
  CPC ..... *A61N 1/36146* (2013.01); *A61N 1/36178* (2013.01); *A61N 1/37247* (2013.01); *G06F 19/3418* (2013.01); *G16H 20/70* (2018.01); *G16H 40/63* (2018.01); *G16H 50/30* (2018.01)

(58) Field of Classification Search
  CPC .............. A61N 1/36135; A61N 1/3606; A61N 1/37247; A61N 1/36003; A61N 1/36007; A61N 1/36046; A61N 1/378; A61N 1/3906; A61N 1/36036; H05K 999/00
  USPC .......................................................... 607/66
  See application file for complete search history.

(56) References Cited

U.S. PATENT DOCUMENTS

| | | | |
|---|---|---|---|
| 4,935,674 A | 6/1990 | Rodriguez-cavazos | |
| 5,300,096 A | 4/1994 | Hall et al. | |
| 5,360,437 A | 11/1994 | Thompson | |
| 5,369,224 A | 11/1994 | Miyata | |
| 5,713,937 A | 2/1998 | Nappholz et al. | |
| 5,724,985 A | 3/1998 | Snell et al. | |
| 5,725,560 A | 3/1998 | Brink | |
| 6,266,566 B1 | 7/2001 | Nichols et al. | |
| 6,516,227 B1 | 2/2003 | Meadows et al. | |
| 6,675,046 B2 | 1/2004 | Holsheimer | |
| 6,895,280 B2 | 5/2005 | Meadows et al. | |
| 6,993,384 B2 | 1/2006 | Bradley et al. | |
| 7,003,349 B1 | 2/2006 | Andersson et al. | |
| 7,228,179 B2 | 6/2007 | Campen et al. | |
| 7,317,948 B1 | 1/2008 | King et al. | |
| 7,333,856 B1 | 2/2008 | Er et al. | |
| 7,333,857 B2 | 2/2008 | Campbell | |
| 7,539,538 B2 | 5/2009 | Parramon et al. | |
| 7,650,184 B2 | 1/2010 | Walter | |
| 7,664,849 B1 | 2/2010 | Chandler et al. | |
| 7,783,353 B2 | 8/2010 | Libbus et al. | |
| 7,826,901 B2 | 11/2010 | Lee et al. | |
| 7,979,119 B2 | 7/2011 | Kothandaraman et al. | |
| 7,979,133 B2 | 7/2011 | Feler et al. | |
| 7,983,762 B2 | 7/2011 | Gliner et al. | |
| 8,019,439 B2 | 9/2011 | Kuzma et al. | |
| 8,224,453 B2 | 7/2012 | De Ridder | |
| 8,255,057 B2 | 8/2012 | Fang et al. | |
| 8,285,389 B2 | 10/2012 | Libbus et al. | |
| 8,340,775 B1 | 12/2012 | Cullen et al. | |
| 8,355,797 B2 | 1/2013 | Caparso et al. | |
| 8,455,716 B2 | 6/2013 | Huang et al. | |
| 8,504,147 B2 | 8/2013 | Deem et al. | |
| 8,560,080 B2 | 10/2013 | Goetz | |
| 8,615,300 B2 | 12/2013 | Feler et al. | |
| 8,649,874 B2 | 2/2014 | Alataris et al. | |
| 8,670,831 B2 | 3/2014 | Wacnik et al. | |
| 8,676,329 B2 | 3/2014 | Wacnik et al. | |
| 8,676,331 B2 | 3/2014 | Parker | |
| 8,692,843 B2 | 4/2014 | Bloemer | |
| 8,694,113 B2 | 4/2014 | Smoorenburg | |
| 8,731,675 B2 | 5/2014 | Ranu et al. | |
| 8,751,009 B2 | 6/2014 | Wacnik | |
| 8,798,755 B2 | 8/2014 | Grill et al. | |
| 8,874,211 B2 | 10/2014 | Libbus et al. | |
| 9,265,948 B2 | 2/2016 | Libbus et al. | |
| 9,737,717 B2 | 8/2017 | Moffitt et al. | |
| 9,802,052 B2 | 10/2017 | Marnfeldt | |
| 2002/0077669 A1 | 6/2002 | Lindh et al. | |
| 2002/0077859 A1 | 6/2002 | Stahmann et al. | |
| 2002/0115939 A1 | 8/2002 | Mulligan et al. | |
| 2003/0139781 A1 | 7/2003 | Bradley et al. | |
| 2003/0176899 A1 | 9/2003 | Samuelsson et al. | |
| 2004/0111131 A1 | 6/2004 | Hu et al. | |
| 2005/0177206 A1 | 8/2005 | North et al. | |
| 2006/0149337 A1 | 7/2006 | John | |
| 2006/0241720 A1 | 10/2006 | Woods et al. | |
| 2007/0150036 A1 | 6/2007 | Anderson | |
| 2007/0299663 A1 | 12/2007 | Fado et al. | |
| 2008/0158175 A1 | 7/2008 | Hotelling et al. | |
| 2008/0163097 A1 | 7/2008 | Goetz et al. | |
| 2008/0188909 A1 | 8/2008 | Bradley | |
| 2009/0024189 A1 | 1/2009 | Lee et al. | |
| 2009/0043359 A1 | 2/2009 | Smoorenburg | |
| 2009/0198305 A1 | 8/2009 | Naroditsky et al. | |
| 2009/0204173 A1 | 8/2009 | Fang et al. | |
| 2010/0010390 A1 | 1/2010 | Skelton et al. | |
| 2010/0010566 A1 | 1/2010 | Thacker et al. | |
| 2010/0010646 A1 | 1/2010 | Drew et al. | |
| 2010/0121409 A1 | 5/2010 | Kothandaraman et al. | |
| 2010/0274312 A1 | 10/2010 | Alataris et al. | |
| 2010/0274314 A1 | 10/2010 | Alataris et al. | |
| 2010/0274315 A1 | 10/2010 | Alataris et al. | |
| 2010/0274317 A1 | 10/2010 | Parker et al. | |
| 2010/0274318 A1 | 10/2010 | Walker et al. | |
| 2010/0274326 A1 | 10/2010 | Chitre et al. | |
| 2011/0208012 A1 | 2/2011 | Gerber et al. | |
| 2011/0054570 A1 | 3/2011 | Lane | |
| 2011/0093051 A1 | 4/2011 | Davis et al. | |
| 2012/0059446 A1 | 3/2012 | Wallace et al. | |
| 2012/0083709 A1 | 4/2012 | Parker et al. | |
| 2012/0109006 A1 | 5/2012 | James et al. | |
| 2012/0197336 A1 | 8/2012 | Su | |
| 2012/0253422 A1 | 10/2012 | Thacker et al. | |
| 2012/0265267 A1 | 10/2012 | Blum et al. | |
| 2012/0265279 A1 | 10/2012 | Zhu et al. | |
| 2012/0283797 A1 | 11/2012 | De Ridder | |
| 2012/0290041 A1 | 11/2012 | Kim et al. | |
| 2012/0296396 A1 | 11/2012 | Moffitt et al. | |
| 2013/0041283 A1 | 2/2013 | Wichner | |
| 2013/0053926 A1 | 2/2013 | Hincapie Ordonez et al. | |
| 2013/0060304 A1 | 2/2013 | Wichner | |
| 2013/0066411 A1 | 3/2013 | Thacker et al. | |
| 2013/0116752 A1 | 5/2013 | Parker et al. | |
| 2013/0131760 A1 | 5/2013 | Rao et al. | |
| 2013/0226261 A1 | 8/2013 | Sparks et al. | |
| 2013/0268021 A1 | 10/2013 | Moffitt | |
| 2013/0268026 A1 | 10/2013 | Rao et al. | |
| 2013/0296975 A1 | 11/2013 | Lee et al. | |
| 2013/0304152 A1 | 11/2013 | Bradley et al. | |
| 2014/0005743 A1 | 1/2014 | Giuffrida et al. | |
| 2014/0052033 A1 | 2/2014 | Lawlis et al. | |
| 2014/0067016 A1 | 3/2014 | Kaula et al. | |
| 2014/0074179 A1 | 3/2014 | Heldman et al. | |
| 2014/0074180 A1 | 3/2014 | Heldman et al. | |
| 2014/0074190 A1 | 3/2014 | Griffith | |
| 2014/0081349 A1 | 3/2014 | Lee et al. | |
| 2014/0081354 A1 | 3/2014 | Davis et al. | |
| 2014/0172045 A1 | 6/2014 | Yip et al. | |
| 2014/0257425 A1 | 9/2014 | Arcot-krishnamurthy et al. | |
| 2014/0257428 A1 | 9/2014 | Zhu | |
| 2014/0276181 A1 | 9/2014 | Sun et al. | |
| 2014/0277267 A1 | 9/2014 | Vansickle et al. | |
| 2015/0012057 A1 | 1/2015 | Carlson et al. | |
| 2015/0051666 A1 | 2/2015 | Roy et al. | |
| 2015/0165209 A1 | 6/2015 | Grandhe et al. | |
| 2015/0224307 A1 | 8/2015 | Bolea | |
| 2015/0238762 A1 | 8/2015 | Pal et al. | |
| 2015/0297893 A1 | 10/2015 | Kokones et al. | |
| 2015/0328461 A1 | 11/2015 | Charlesworth et al. | |
| 2015/0328462 A1 | 11/2015 | Griffith | |
| 2015/0328467 A1 | 11/2015 | Demers et al. | |
| 2015/0343242 A1 | 12/2015 | Tyler et al. | |
| 2016/0027293 A1 | 1/2016 | Esteller et al. | |
| 2016/0074662 A1 | 3/2016 | Moffitt et al. | |
| 2016/0074663 A1 | 3/2016 | De Ridder | |
| 2016/0121126 A1 | 5/2016 | Marnfeldt | |
| 2016/0279429 A1 | 9/2016 | Hershey et al. | |

(56) References Cited

U.S. PATENT DOCUMENTS

| | | | | |
|---|---|---|---|---|
| 2017/0050033 | A1* | 2/2017 | Wechter | A61N 1/0556 |
| 2017/0333718 | A1 | 11/2017 | Moffitt et al. | |

FOREIGN PATENT DOCUMENTS

| | | | |
|---|---|---|---|
| CN | 106687173 | A | 5/2017 |
| CN | 107073269 | A | 8/2017 |
| CN | 107921255 | A | 4/2018 |
| CN | 108463266 | A | 8/2018 |
| JP | 1057508 | A | 3/1998 |
| JP | 2010534114 | A | 11/2010 |
| JP | 2013533092 | A | 8/2013 |
| JP | 2014518722 | A | 8/2014 |
| JP | 2017527429 | A | 9/2017 |
| JP | 2017533072 | A | 11/2017 |
| WO | WO-03051175 | A2 | 6/2003 |
| WO | WO-3051175 | A2 | 6/2003 |
| WO | WO-2006029257 | A2 | 3/2006 |
| WO | WO-2006135791 | A2 | 12/2006 |
| WO | WO-2009067610 | A1 | 5/2009 |
| WO | WO-2014159880 | A1 | 10/2014 |
| WO | WO-2016004230 | A1 | 1/2016 |
| WO | WO-2016044169 | A1 | 3/2016 |
| WO | WO-2016073271 | A1 | 5/2016 |
| WO | WO-2016154375 | A1 | 9/2016 |
| WO | WO-2016172239 | A1 | 10/2016 |
| WO | WO-2017019191 | A1 | 2/2017 |
| WO | WO-2017066187 | A1 | 4/2017 |

OTHER PUBLICATIONS

"International Application Serial No. PCT/US2015/58017, International Search Report dated Apr. 6, 2016", 5 pgs.

"International Application Serial No. PCT/US2015/58017, Written Opinion dated Apr. 6, 2016", 8 pgs.

"International Application Serial No. PCT/US2015/049993, International Search Report dated Jan. 14, 2016", 3 pgs.

"International Application Serial No. PCT/US2015/049993, Written Opinion dated Jan. 14, 2016", 4 pgs.

"International Application Serial No. PCT/US2016/023888, International Search Report dated Jun. 6, 2016", 5 pgs.

"International Application Serial No. PCT/US2016/023888, Written Opinion dated Jun. 6, 2016", 5 pgs.

"International Application Serial No. PCT/US2016/037226, International Search Report dated Aug. 25, 2016", 4 pgs.

"International Application Serial No. PCT/US2016/037226, Written Opinion dated Aug. 25, 2016", 5 pgs.

Moffitt, Michael A., et al., "Graphical User Interface for Programming Neurostimulation Pulse Patterns", U.S. Appl. No. 14/853,589, filed Sep. 14, 2015.

Rao, Prakash, et al., "Technique for Linking Electrodes Together During Programming of Neurostimulation System", U.S. Appl. No. 61/561,760, filed Nov. 18, 2011.

Vansickle, Dennis Allen, et al., "Neuromodulation System and Method for Transitioning Between Programming Modes", U.S. Appl. No. 14/214,752, filed Mar. 15, 2014.

Vansickle, Dennis Allen, "Systems and Methods for Delivering Sub-Threshold Therapy to a Patient", U.S. Appl. No. 61/801,917, filed Mar. 15, 2013.

"U.S. Appl. No. 14/853,589, Final Office Action dated Jan. 18, 2017", 12 pgs.

"U.S. Appl. No. 14/853,589, Notice of Allowance dated Apr. 17, 2017", 5 pgs.

"U.S. Appl. No. 14/853,589, Response filed Mar. 14, 2017 to Final Office Action dated Jan. 18, 2017", 12 pgs.

"U.S. Appl. No. 14/853,589, Response filed Nov. 17, 2016 to Non Final Office Action dated Aug. 17, 2016", 12 pgs.

"U.S. Appl. No. 14/926,725, Corrected Notice of Allowance dated Jul. 17, 2017", 2 pgs.

"U.S. Appl. No. 14/926,725, Non Final Office Action dated Mar. 3, 2017", 13 pgs.

"U.S. Appl. No. 14/926,725, Notice of Allowability dated Jul. 28, 2017", 2 pgs.

"U.S. Appl. No. 14/926,725, Notice of Allowance dated Jun. 27, 2017", 8 pgs.

"U.S. Appl. No. 14/926,725, Response filed May 25, 2017 to Non Final Office Action dated Mar. 3, 2017", 12 pgs.

"U.S. Appl. No. 15/079,340, Advisory Action dated Jun. 21, 2018", 3 pgs.

"U.S. Appl. No. 15/079,340, Final Office Action dated Apr. 4, 2018", 12 pgs.

"U.S. Appl. No. 15/079,340, Non Final Office Action dated Jul. 27, 2018", 12 pgs.

"U.S. Appl. No. 15/079,340, Non Final Office Action dated Oct. 3, 2017", 10 pgs.

"U.S. Appl. No. 15/079,340, Response filed Jun. 4, 2018 to Final Office Action dated Apr. 4, 2018", 10 pgs.

"U.S. Appl. No. 15/079,340, Response filed Dec. 20, 2017 to Non Final Office Action dated Oct. 3, 2017", 10 pgs.

"U.S. Appl. No. 15/180,980, Advisory Action dated May 24, 2018", 5 pgs.

"U.S. Appl. No. 15/180,980, Examiner Interview Summary dated Apr. 30, 2018", 3 pgs.

"U.S. Appl. No. 15/180,980, Final Office Action dated Mar. 1, 2018", 10 pgs.

"U.S. Appl. No. 15/180,980, Non Final Office Action dated Jul. 19, 2018", 10 pgs.

"U.S. Appl. No. 15/180,980, Non Final Office Action dated Sep. 21, 2017", 9 pgs.

"U.S. Appl. No. 15/180,980, Repsonse filed Dec. 20, 2017 to Non Final Office Action dated Sep. 21, 2017", 15 pgs.

"U.S. Appl. No. 15/180,980, Response filed Jul. 2, 2018 to Advisory Action dated May 24, 2018", 11 pgs.

"Australian Application Serial No. 2015318142, First Examiners Report dated Sep. 15, 2017", 3 pgs.

"Australian Application Serial No. 2015318142, Response filed Feb. 8, 2018 to First Examiners Report dated Sep. 15, 2017", 15 pgs.

"Australian Application Serial No. 2015343483, First Examiners Report dated Sep. 19, 2017", 3 pgs.

"Australian Application Serial No. 2015343483, Response filed Feb. 8, 2018 to First Examiners Report dated Sep. 19, 2017", 17 pgs.

"Australian Application Serial No. 2016297965, First Examination Report dated Jun. 19, 2018", 3 pgs.

"Chinese Application Serial No. 201580048568.3, Office Action dated Jul. 31, 2018", with English translation, 24 pgs.

"European Application Serial No. 15767069.6, Response filed Nov. 23, 2017 to Communication Pursuant to Rules 161 and 162 EPC dated May 19, 2017", 12 pgs.

"European Application Serial No. 15791183.5, Response filed Feb. 6, 2018 to Communication Pursuant to Rules 161 & 162 EPC dated Jul. 27, 2017", 12 pgs.

"International Application Serial No. PCT/US2015/049993, International Preliminary Report on Patentability dated Mar. 30, 2017", 6 pgs.

"International Application Serial No. PCT/US2015/058017, International Preliminary Report on Patentability dated May 18, 2017", 10 pgs.

"International Application Serial No. PCT/US2016/023888, International Preliminary Report on Patentability dated Oct. 5, 2017", 7 pgs.

"International Application Serial No. PCT/US2016/037226, International Preliminary Report on Patentability dated Feb. 8, 2018", 7 pgs.

"International Application Serial No. PCT/US2016/056426, International Preliminary Report on Patentability dated Apr. 26, 2018", 8 pgs.

"International Application Serial No. PCT/US2016/056426, International Search Report dated Jan. 26, 2017", 5 pgs.

"International Application Serial No. PCT/US2016/056426, Written Opinion dated Jan. 26, 2017", 6 pgs.

(56) References Cited

OTHER PUBLICATIONS

"Japanese Application Serial No. 2017-533728, Office Action dated Jan. 11, 2018", With English Translation, 9 pgs.

"Japanese Application Serial No. 2017-542797, Office Action dated May 21, 2018", with English translation, 4 pgs.

"Japanese Application Serial No. 2017-542797, Response filed Aug. 17, 2018 to Office Action dated May 21, 2018", w/ English claims, 9 pgs.

U.S. Appl. No. 15/670,328, filed Aug. 7, 2017, Graphical User Interface for Programming Neurostimulation Pulse Patterns.

U.S. Appl. No. 14/926,725, filed Oct. 29, 2015, Method and Apparatus for Programming Complex Neurostimulation Patterns, U.S. Pat. No. 9,802,052.

U.S. Appl. No. 15/079,340, filed Mar. 24, 2016, Method and Apparatus for Controlling Temporal Patterns of Neurostimulation.

U.S. Appl. No. 15/180,980, filed Jun. 13, 2016, User Interface for Custom Patterned Electrical Stimulation.

\* cited by examiner

| Composer 🖉 | Library | Pulses | Burst | Trains | Sequences | ○ ON \| OFF | ⟳ Sync to IPG |

Default Library
Standard stimulations from Boston Scientific Inc.                    🖉Edit  📇Export  📑Duplicate  🗑Trash

| | Ref | Kind | Name | Preview | Dependencies | |
|---|---|---|---|---|---|---|
| ☐ | P1 | Pulse | Tonic | | - | 🖉Edit |
| ☑ | T1 | Train | CR BSCI | | - | 🖉Edit |
| ☐ | B1 | Burst | Stochastic | | P2, P3, P4 | 🖉Edit |
| ☐ | S1 | Sequence | UCSF Protocol 2A - Dr. McKessen | | - | 🖉Edit |
| ☐ | P1 | Pulse | Biphasic | | - | 🖉Edit |
| ☑ | T1 | Train | CR BSCI II | | P2, P3, B1 | 🖉Edit |
| ☐ | B1 | Burst | UCSF Protocol 2A - Dr. Kelly | | - | 🖉Edit |
| ☐ | S1 | Sequence | Clinical Trial II | | - | 🖉Edit |

Programmer Library
Custom configurations shared across patient.                     🖉Edit  📇Export  📑Duplicate  🗑Trash

| | Ref | Kind | Name | Preview | Dependencies | |
|---|---|---|---|---|---|---|
| ☐ | P1 | Pulse | UCSF Protocol 2A - Dr. McKessen | | - | 🖉Edit |
| ☑ | T1 | Train | UCSF Protocol 2A - Dr. Lubensky | | - | 🖉Edit |
| ☐ | B1 | Burst | UCSF Protocol 2A - Dr. McKessen | | - | 🖉Edit |
| ☐ | S1 | Sequence | UCSF Protocol 2A - Dr. McKessen | | - | 🖉Edit |

Patient Library
Custom configurations specific to a patient.                     🖉Edit  📇Export  📑Duplicate  🗑Trash

| | Ref | Kind | Name | Preview | Dependencies | |
|---|---|---|---|---|---|---|
| ☐ | P1 | Pulse | Tonic | | - | 🖉Edit |
| ☑ | T1 | Train | CR BSCI | | - | 🖉Edit |
| ☐ | B1 | Burst | Stochastic | | - | 🖉Edit |
| ☐ | S1 | Sequence | UCSF Protocol 2A - Dr. McKessen | | - | 🖉Edit |

*FIG. 9*

| Composer | Library | Pulses | Burst | Trains | Sequences | | | | Exit |
|---|---|---|---|---|---|---|---|---|---|
| Library Pulses, Burst, Trains, Sequences | Filter | | | | | +New | | | |

| Select | Type | Note | Title | Preview | Freq | Pw | Strategy | Source | Date Edited | Actions |
|---|---|---|---|---|---|---|---|---|---|---|
| ☐ | Pulse | ⓘ | Tonic Regular | ⎍ | — | 55ms | Sub Perception | Boston Scientific | 1.12.2015 | ▾≡ |
| ☑ | Pulse | ⓘ | Tonic Regular | ⎍ | — | 55ms | Sub Perception | Custom | 1.12.2015 | ▾≡ |
| ☐ | Pulse | ⓘ | Tonic High | ⎍ | — | 55ms | Sub Perception | Stanford | 1.12.2015 | ▾≡ |
| ☐ | Pulse | ⓘ | Tonic Regular | ⎍ | — | 55ms | Normal | Boston Scientific | 1.12.2015 | ▾≡ |
| ☐ | Pulse | ⓘ | Tonic Regular | ⎍ | — | 55ms | Sub Perception | Custom | 1.12.2015 | ▾≡ |
| ☐ | Pulse | ⓘ | Tonic High | ⎍ | — | 55ms | Normal | Stanford | 1.12.2015 | ▾≡ |
| ☐ | Pulse | ⓘ | Tonic High | ⎍ | — | 55ms | Normal | Stanford | 1.12.2015 | ▾≡ |
| ☐ | Pulse | ⓘ | Tonic Regular | ⎍ | — | 55ms | Normal | Boston Scientific | 1.12.2015 | ▾≡ |
| ☐ | Pulse | ⓘ | Tonic Regular | ⎍ | — | 55ms | Normal | Custom | 1.12.2015 | ▾≡ |
| ☐ | Pulse | ⓘ | Tonic High | ⎍ | — | 55ms | Sub Perception | Stanford | 1.12.2015 | ▾≡ |
| ☐ | Burst | ⓘ | High Rate II | ∥∥∥∥∥∥ | 55hz | 55ms | Sub Perception | Custom | 1.12.2015 | ▾≡ |
| ☐ | Burst | ⓘ | High Rate III | ∥∥∥∥∥∥ | 55-75hz | 55ms | Sub Perception | Custom | 1.12.2015 | ▾≡ |
| ☐ | Burst | ⓘ | Custom HR | ∥∥∥∥∥∥ | 55-75hz | 55ms | Sub Perception | Boston Scientific | 1.12.2015 | ▾≡ |
| ☐ | Burst | ⓘ | Custom HR | ∥∥∥∥∥∥ | 55hz | 55ms | Sub Perception | Custom | 1.12.2015 | ▾≡ |
| ☐ | Burst | ⓘ | Custom HR | ∥∥∥∥∥∥ | 55hz | 55ms | Sub Perception | Stanford | 1.12.2015 | ▾≡ |
| ☐ | Train | ⓘ | Train Title | ∥∥∥∥∥∥ | 55-75hz | 55ms | Normal | Boston Scientific | 1.12.2015 | ▾≡ |
| ☐ | Train | ⓘ | Train Title | ∥∥∥∥∥∥ | 55-75hz | 55ms | Sub Perception | Custom | 1.12.2015 | ▾≡ |
| ☐ | Train | ⓘ | Train Title | ∥∥∥∥∥∥ | 55-75hz | 55ms | Normal | Stanford | 1.12.2015 | ▾≡ |
| ☐ | Train | ⓘ | Train Title | ∥∥∥∥∥∥ | 55-75hz | 55ms | Sub Perception | Boston Scientific | 1.12.2015 | ▾≡ |
| ☐ | Sequence | ⓘ | Trail I | ▊▊▊▊ | 1000hz | 55ms | High Rate | Stanford | 1.12.2015 | ▾≡ |
| ☐ | Sequence | ⓘ | Trail II | ▊▊▊▊ | 55hz | 55ms | Sub Perception | Boston Scientific | 1.12.2015 | ▾≡ |
| ☐ | Sequence | ⓘ | Parkinson Protocol I | ▊▊▊▊ | 55hz | 55ms | Sub Perception | Custom | 1.12.2015 | ▾≡ |
| ☐ | Sequence | ⓘ | Parkinson Protocol II | ▊▊▊▊ | 1200hz | 55ms | High Rate | Stanford | 1.12.2015 | ▾≡ |
| ☐ | Sequence | ⓘ | Sequence Title | ▊▊▊▊ | 55hz | 55ms | Sub Perception | Boston Scientific | 1.12.2015 | ▾≡ |

*FIG. 21*

| Composer | | | Library | Pulses | Burst | Trains | Sequences | | Exit |
|---|---|---|---|---|---|---|---|---|---|
| Pulses A single waveform | | | Filter ▼≡ | 🔍 | | | +New Pulse | ✎ 📋 📑 🗑 | |
| Select | Type | Title | Preview | Freq | Pw | Strategy | Source | Date Edited | Actions |
| ☐ | Pulse | Tonic Regular | ⊓⌐ | -- | 120ms | Sub Perception | Boston Scientific | 1.12.2015 | ▼≡ |
| ☐ | Pulse | Tonic Regular | ⊓⌐ | -- | 120ms | Sub Perception | Custom | 1.12.2015 | ▼≡ |
| ☐ | Pulse | Tonic High | ⊓⌐ | -- | 120ms | Sub Perception | Stanford | 1.12.2015 | ▼≡ |
| ☐ | Pulse | Tonic Regular | ⊓⌐ | -- | 120ms | Sub Perception | Boston Scientific | 1.12.2015 | ▼≡ |
| ☐ | Pulse | Tonic Regular | ⊓⌐ | -- | 120ms | Sub Perception | Custom | 1.12.2015 | ▼≡ |
| ☐ | Pulse | Tonic High | ⊓⌐ | -- | 120ms | Sub Perception | Stanford | 1.12.2015 | ▼≡ |
| ☐ | Pulse | Tonic Regular | ⊓⌐ | -- | 120ms | Sub Perception | Boston Scientific | 1.12.2015 | ▼≡ |
| ☐ | Pulse | Tonic Regular | ⊓⌐ | -- | 120ms | Sub Perception | Custom | 1.12.2015 | ▼≡ |
| ☐ | Pulse | Tonic High | ⊓⌐ | -- | 120ms | Sub Perception | Stanford | 1.12.2015 | ▼≡ |

*FIG. 22*

| Composer | | | Library | Pulses | Burst | Trains | Sequences | | Exit |
|---|---|---|---|---|---|---|---|---|---|
| Bursts Burst are a series of pulses | | | Filter ▼≡ | 🔍 | | | +New Burst | | ✏ 📋 📁 🗑 |

| Select | Type | Title | Preview | Freq | Pw | Strategy | Source | Date Edited | Actions |
|---|---|---|---|---|---|---|---|---|---|
| ☐ | Burst | Constant Toxic | ‖‖‖‖‖‖‖— | 55hz | 55hz | Sub Perception | Boston Scientific | 1.12.2015 | ▼≡ |
| ☑ | Burst | Decending | ‖‖‖‖‖‖‖ | 55hz | 55hz | Sub Perception | Custom | 1.12.2015 | ▼≡ |
| ☐ | Burst | Normal | ‖‖‖‖‖‖— | 55hz | 100hz | Sub Perception | Stanford | 1.12.2015 | ▼≡ |
| ☐ | Burst | High Rate I | ‖‖‖‖‖‖‖— | 55hz | 1000hz | High rate | Boston Scientific | 1.12.2015 | ▼≡ |
| ☐ | Burst | High Rate II | ‖‖‖‖‖‖‖ | 55hz | 55hz | High rate | Custom | 1.12.2015 | ▼≡ |
| ☐ | Burst | High Rate III | ‖‖‖‖‖— | 55hz | 55hz | High rate | Stanford | 1.12.2015 | ▼≡ |
| ☐ | Burst | Custom HR | ‖‖‖‖‖‖— | 55hz | 55hz | Sub Perception | Boston Scientific | 1.12.2015 | ▼≡ |
| ☐ | Burst | Custom HR | ‖‖‖‖‖‖‖ | 55hz | 55hz | Sub Perception | Custom | 1.12.2015 | ▼≡ |
| ☐ | Burst | Custom HR | ‖‖‖‖‖— | 55hz | 55hz | Sub Perception | Stanford | 1.12.2015 | ▼≡ |

*FIG. 24*

| Composer | | | Library | Pulses | Burst | Trains | Sequences | | Exit |
|---|---|---|---|---|---|---|---|---|---|

Trains  Trains are a series of bursts   [Filter ▼≡] [🔍  ]  [+ New Pulse]  [✎ 💾 🗐 🗑]

| Select | Type | Title | Preview | Freq | Pw | Strategy | Source | Date Edited | Actions |
|---|---|---|---|---|---|---|---|---|---|
| ☐ | Train | Train Title | ‖‖‖‖‖ ‖‖ ‖ | 55hz | 55hz | Sub Perception | Boston Scientific | 1.12.2015 | ▼≡ |
| ☐ | Train | Train Title | ‖‖‖‖‖ ‖‖ ‖ | 55hz | 55hz | Sub Perception | Custom | 1.12.2015 | ▼≡ |
| ☐ | Train | Train Title | ‖‖‖‖‖ ‖‖ ‖ | 55hz | 55hz | Sub Perception | Stanford | 1.12.2015 | ▼≡ |
| ☐ | Train | Train Title | ‖‖‖‖‖ ‖‖ ‖ | 55hz | 55hz | Sub Perception | Boston Scientific | 1.12.2015 | ▼≡ |
| ☐ | Train | Train Title | ‖‖‖‖‖ ‖‖ ‖ | 55hz | 55hz | Sub Perception | Custom | 1.12.2015 | ▼≡ |
| ☐ | Train | Train Title | ‖‖‖‖‖ ‖‖ ‖ | 55hz | 55hz | Coordinated Reset | Stanford | 1.12.2015 | ▼≡ |
| ☐ | Train | Train Title | ‖‖‖‖‖ ‖‖ ‖ | 55hz | 55hz | Coordinated Reset | Boston Scientific | 1.12.2015 | ▼≡ |
| ☐ | Train | Train Title | ‖‖‖‖‖ ‖‖ ‖ | 55hz | 55hz | Coordinated Reset | Custom | 1.12.2015 | ▼≡ |
| ☐ | Train | Tonic High | ‖‖‖‖‖ ‖‖ ‖ | 55hz | 55hz | Coordinated Reset | Stanford | 1.12.2015 | ▼≡ |

*FIG. 26*

| Composer | | Library | Pulses | Burst | Trains | Sequences | | Exit | |
|---|---|---|---|---|---|---|---|---|---|
| Sequences | A combination of pulses, burst, trains and puases. | Filter ▼≡ | Q | | | | +New Pulse | ✎ 📋 📄 🗑 | |

| Select | Type | Title | Preview | Freq | Pw | Strategy | Source | Date Edited | Actions |
|---|---|---|---|---|---|---|---|---|---|
| ☐ | Sequence | Sequence Title | ▨▨▨ | 55hz | 55hz | Sub Perception | Boston Scientific | 1.12.2015 | ▼≡ |
| ☑ | Sequence | Sequence Title | ▨▨▨ | 55hz | 55hz | Sub Perception | Custom | 1.12.2015 | ▼≡ |
| ☐ | Sequence | Trial I | ▨▨▨ | 55hz | 55hz | Sub Perception | Stanford | 1.12.2015 | ▼≡ |
| ☐ | Sequence | Trial II | ▨▨▨ | 55hz | 55hz | Sub Perception | Boston Scientific | 1.12.2015 | ▼≡ |
| ☐ | Sequence | Parkinson Protocol I | ▨▨▨ | 55hz | 55hz | Sub Perception | Custom | 1.12.2015 | ▼≡ |
| ☐ | Sequence | Parkinson Protocol II | ▨▨▨ | 55hz | 55hz | Coordinated Reset | Stanford | 1.12.2015 | ▼≡ |
| ☐ | Sequence | Sequence Title | ▨▨▨ | 55hz | 55hz | Coordinated Reset | Boston Scientific | 1.12.2015 | ▼≡ |
| ☐ | Sequence | Sequence Title | ▨▨▨ | 55hz | 55hz | Coordinated Reset | Custom | 1.12.2015 | ▼≡ |
| ☐ | Sequence | Sequence Title | ▨▨▨ | 55hz | 55hz | Coordinated Reset | Stanford | 1.12.2015 | ▼≡ |

*FIG. 29*

USER INTERFACE FOR NEUROSTIMULATION WAVEFORM COMPOSITION

CLAIM OF PRIORITY

This application claims the benefit of priority under 35 U.S.C. § 119(e) of U.S. Provisional Patent Application Ser. No. 62/241,965, filed on Oct. 15, 2015, and U.S. Provisional Patent Application Ser. No. 62/333,551, filed on May 9, 2016 each of which is herein incorporated by reference in its entirety.

TECHNICAL FIELD

This document relates generally to medical devices and more particularly to a user interface for neurostimulation programming including composition of stimulation waveforms.

BACKGROUND

Neurostimulation, also referred to as neuromodulation, has been proposed as a therapy for a number of conditions. Examples of neurostimulation include Spinal Cord Stimulation (SCS), Deep Brain Stimulation (DBS), Peripheral Nerve Stimulation (PNS), and Functional Electrical Stimulation (FES). Implantable neurostimulation systems have been applied to deliver such a therapy. An implantable neurostimulation system may include an implantable neurostimulator, also referred to as an implantable pulse generator (IPG), and one or more implantable leads each including one or more electrodes. The implantable neurostimulator delivers neurostimulation energy through one or more electrodes placed on or near a target site in the nervous system. An external programming device is used to program the implantable neurostimulator with stimulation parameters controlling the delivery of the neurostimulation energy.

In one example, the neurostimulation energy is delivered in the form of electrical neurostimulation pulses. The delivery is controlled using stimulation parameters that specify spatial (where to stimulate), temporal (when to stimulate), and informational (patterns of pulses directing the nervous system to respond as desired) aspects of a pattern of neurostimulation pulses. Many current neurostimulation systems are programmed to deliver periodic pulses with one or a few uniform waveforms continuously or in bursts. However, the human nervous systems use neural signals having much more sophisticated patterns to communicate various types of information, including sensations of pain, pressure, temperature, etc. The nervous system may interpret an artificial stimulation with a simple pattern of stimuli as an unnatural phenomenon, and respond with an unintended and undesirable sensation and/or movement. For example, some neurostimulation therapies are known to cause paresthesia and/or vibration of non-targeted tissue or organ.

Recent research has shown that the efficacy and efficiency of certain neurostimulation therapies can be improved, and their side-effects can be reduced, by using patterns of neurostimulation pulses that emulate natural patterns of neural signals observed in the human body. While modern electronics can accommodate the need for generating such sophisticated pulse patterns, the capability of a neurostimulation system depends on its post-manufacturing programmability to a great extent. For example, a sophisticated pulse pattern may only benefit a patient when it is customized for that patient, and stimulation patterns predetermined at the time of manufacturing may substantially limit the potential for the customization. Such customization may be performed at least in part by a user such as a physician or other caregiver with the patient in a clinical setting.

SUMMARY

An example (e.g., "Example 1") of a system for use by a user to program a neurostimulator configured to deliver neurostimulation to a patient may include a first storage device and a first user interface. The first storage device may be configured to store waveform building blocks. The first user interface may include a first display screen, a first user input device, and a first interface control circuit coupled to the first display screen and the first user input device. The first interface control circuit may include a waveform composer configured to allow for composition of one of more building blocks of the waveform building blocks and composition of a pattern of the neurostimulation pulses using one of more building blocks selected from the waveform building blocks. The waveform composer may include a library controller and a plurality of waveform building block editors. The library controller may be configured to display a library management area on the screen. The displayed library management area allows the user to manage the waveform building blocks stored in the storage device. The waveform building block editors may each be configured to allow the user to compose a type of the waveform building blocks of a plurality of types of the waveform building blocks.

In Example 2, the subject matter of Example 1 may optionally be configured to further include a programming control circuit configured to generate a plurality of stimulation parameters controlling delivery of neurostimulation pulses from the neurostimulator according to the pattern of the neurostimulation pulses.

In Example 3, the subject matter of Example 2 may optionally be configured to further include a remote device and an external programming device. The remote device includes the first storage device and the first user interface. The external programming device includes the programming control circuit.

In Example 4, the subject matter of Example 3 may optionally be configured such that the external programming device is configured to import one or more of one or more waveform building blocks of the waveform building blocks or the pattern of the neurostimulation pulses from the remote device. The external programming device includes a second user interface including a second display screen, a second user input device, and a second interface control circuit coupled to the second display screen and the second user input device. The second interface control circuit includes a stimulation adjuster configured to allow for adjustment of the imported one or more of the one or more waveform building blocks of the waveform building blocks or the pattern of the neurostimulation pulses.

In Example 5, the subject matter of any one or any combination of Examples 1 to 4 may optionally be configured such that the waveform composer is configured to allow the delivery of the neurostimulation pulses to be turned on and off by the user during the composition of the one or more building blocks of the waveform building blocks and during the composition of the pattern of the neurostimulation pulses.

In Example 6, the subject matter of any one or any combination of Examples 1 to 5 may optionally be configured such that the waveform composer is configured to allow one of the library controller and editors of the plurality of waveform building block editors to be selected by the user for access one at a time.

In Example 7, the subject matter of Example 6 may optionally be configured such that the library controller is configured to display the library management area on the screen in response to a user selection for access to the library controller, and the library management area displays the waveform building blocks each selectable for editing by a corresponding editor of the plurality of waveform building block editors.

In Example 8, the subject matter of Example 7 may optionally be configured such that the library controller is further configured to allow for importation of a new waveform building block to be added to the waveform building blocks in the first storage device.

In Example 9, the subject matter of Example 8 may optionally be configured such that the library controller is further configured to allow for exportation of a waveform building block selected from the waveform building blocks in the first storage device.

In Example 10, the subject matter of any one or any combination of Examples 6 to 9 may optionally be configured such that each editor of the plurality of waveform building block editors is configured to display a library area on the first screen in response to a user request for access to that editor. The library area lists available waveform building blocks of a type of the waveform building blocks of the plurality of types of the waveform building blocks.

In Example 11, the subject matter of Example 10 may optionally be configured such that each editor is configured to display a composition area for the type of the waveform building blocks on the first screen in response to a waveform building block being selected from the listed waveform building blocks. The composition area allows the user to edit the selected waveform building block or to create a new building block to be added to the waveform building blocks stored in the first storage device.

In Example 12, the subject matter of any one or any combination of Examples 6 to 11 may optionally be configured such that the plurality of waveform building block editors includes a pulse editor configured to display a pulse composition area on the first screen in response to a user selection for access to the pulse editor. The pulse composition area allows the user to compose a pulse of the waveform building blocks.

In Example 13, the subject matter of Example 12 may optionally be configured such that the plurality of waveform building block editors includes a burst editor configured to display a burst composition area on the first screen in response to a user selection for access to the burst editor. The burst composition area allows the user to compose a burst of the waveform building blocks, the burst including a group of the pulses.

In Example 14, the subject matter of Example 13 may optionally be configured such that the plurality of waveform building block editors includes a train editor configured to display a train composition area on the first screen in response to a user selection for access to the train editor. The train composition area allows the user to compose a train of the waveform building blocks, the train including a group of the bursts.

In Example 15, the subject matter of Example 14 may optionally be configured such that the plurality of waveform building block editors includes a sequence editor configured to display a sequence composition area on the first screen in response to a user selection for access to the sequence editor. The sequence composition area allows the user to compose a sequence of the waveform building blocks, the sequence including a group of the pulses, bursts, and trains.

An example (e.g., "Example 16") of a method for operating an external system for programming an implantable neurostimulation device is also provided. The method may include storing waveform building blocks in a storage device of the external system and allowing a user to perform waveform composition using a user interface of the external system. The waveform composition may include composition of one of more building blocks of the waveform building blocks and composition of a pattern of the neurostimulation pulses using one of more building blocks selected from the waveform building blocks. Allowing the user to perform the waveform composition may include displaying a library management area on a screen of the user interface and allowing the user to select a waveform building block from the stored waveform building blocks and edit the selected waveform building block using the user input device. The displayed library management area may allow the user to manage the stored waveform building blocks using a user input device of the user interface.

In Example 17, the subject matter of Example 16 may optionally include allowing the user to perform the waveform composition using a remote device of the external system, and further include allowing another user to adjust the composed one of more building blocks of the waveform building blocks and the composed pattern of the neurostimulation pulses using an external programming device of the external system, the external programming device communicatively coupled to the remote device.

In Example 18, the subject matter of Example 17 may optionally further include generating a plurality of stimulation parameters controlling delivery of neurostimulation pulses from the neurostimulator according to the pattern of the neurostimulation pulses using the external programming device.

In Example 19, the subject matter of allowing the user to select the waveform building block from the stored waveform building blocks and edit the selected waveform building block as found in Example 16 may optionally include displaying a library area for a type of the waveform building blocks of a plurality of types of the waveform building blocks on the screen and displaying a composition area for the type of the waveform building blocks on the screen in response to the selection of the building block of the type of the waveform building blocks. The displayed library area allows the user to select a building block of the type of the waveform building blocks using the user input device. The displayed composition area allows the user to edit the selected building block of the type of the waveform building blocks using the user input device.

In Example 20, the subject matter of displaying the composition area as found in Example 19 may optionally further include displaying the composition area to allow the user to create a new building block to be added to the stored waveform building blocks.

In Example 21, the subject matter of Example 20 may optionally further include allowing the user to create a new building block to be added to the stored waveform building blocks, to import a building block to be added to the stored waveform building blocks, and to export a building block selected from the stored waveform building blocks.

In Example 22, the plurality of types of the waveform building blocks as found in Example 19 may optionally include pulses, bursts each including a group of the pulses, trains each including a group of the bursts, and sequences each including a group of the pulses, the bursts, and the trains.

This Summary is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

The drawings illustrate generally, by way of example, various embodiments discussed in the present document. The drawings are for illustrative purposes only and may not be to scale.

FIG. 9 illustrates an embodiment of a screen of a user interface of an external programming device, such as the external programming device of FIG. 6, with a library management area displayed.

FIG. 21 illustrates an embodiment of a screen of a user interface of a remote device, such as the remote device of FIG. 19, with a library management area displayed.

FIG. 22 illustrates an embodiment of the screen of FIG. 21 displaying a pulse library area.

FIG. 24 illustrates an embodiment of the screen of the remote device displaying a burst library area.

FIG. 26 illustrates an embodiment of the screen of the remote device displaying a train library area.

FIG. 29 illustrates an embodiment of the screen of the remote device displaying a sequence library area.

DETAILED DESCRIPTION

Figure 1:
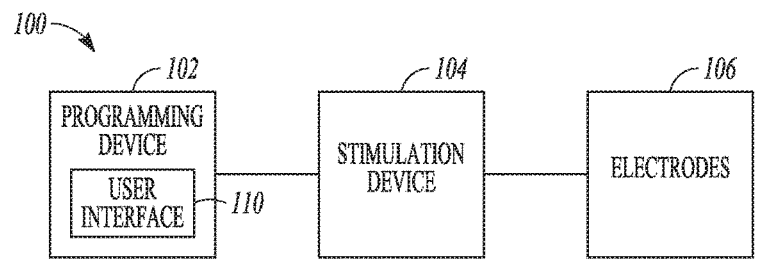
FIG. 1 illustrates an embodiment of a neurostimulation system.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. References to "an", "one", or "various" embodiments in this disclosure are not necessarily to the same embodiment, and such references contemplate more than one embodiment. The following detailed description provides examples, and the scope of the present invention is defined by the appended claims and their legal equivalents.

This document discusses a method and system for programming neurostimulation pulse patterns using a user interface, such as a graphical user interface (GUI). Advancements in neuroscience and neurostimulation research have led to a demand for using complex and/or individually optimized patterns of neurostimulation pulses for various types of therapies. The capability of a neurostimulation system in treating various types of disorders will be limited by the programmability of such patterns of neurostimulation pulses. In various embodiments, the present system allows for custom definition of a pattern of neurostimulation pulses, which includes custom definition of waveforms being the building blocks of the pattern. Such custom definition is achieved by using a user interface that makes it possible for the user to perform the custom definition of potentially very complex patterns of neurostimulation pulses by creating and editing graphical representations of relatively simple individual building blocks for each of the patterns. In various embodiments, the individually definable waveforms may include pulses, bursts of pulses, trains of bursts, and sequences of pulses, bursts, and trains. In various embodiments, the present system provides for patterns of neurostimulation pulses not limited to waveforms predefined at the time of manufacturing, thereby accommodating need for customization of neurostimulation pulse patterns as well as need for new types of neurostimulation pulse patterns that may, for example, result from future research in neurostimulation. This may also facilitate design of a general-purpose neurostimulation device that can be configured by a user for delivering specific types of neurostimulation therapies by programming the device using the user interface.

In various embodiments, the present system includes a neurostimulator programming device with a user interface that enables users to understand, manage, and program stimulation and create patterns of stimuli. Users of the programming device can have different levels of knowledge and expertise with respect to different aspects of programming a neurostimulator, as well as different needs and constraints. Examples include: a physician in an operation room may have very limited time for programming a neurostimulator for a patient under surgery; an academic researcher may have limited understanding of electrical engineering aspects of the stimulation; some users want to know what the stimuli look like; and some users may have limited understanding of anatomy, neuromodulation, and how electrical stimulation actually works. Therefore, the user interface provides access to different levels of access to various aspects of neurostimulation programming to reduce distraction, ensure accuracy and patient safety, and increase efficiency during programming of a neurostimulator.

In various embodiments, the user interface allows for neurostimulation programming starting with templates/presets to enable valuable time savings in defining stimulation waveforms. In various embodiments, the user interface provides for complete editorial control as well as simplified, guided, and template-based editorial options. In various embodiments, the user interface provides the user with interpretation of editorial features and guide rails.

In various embodiments, the present system may be implemented using is a combination of hardware and software designed to provide users such as researchers, physicians or other caregivers, or neurostimulation device makers with ability to create custom waveforms and patterns in an effort to increase therapeutic efficacy and/or patient satisfaction for neurostimulation therapies, including but not being limited to deep brain stimulation (DBS), spinal cord stimulation (SCS), peripheral nerve stimulation (PNS), and vagus nerve stimulation (VNS). While neurostimulation is specifically discussed as an example, the present subject matter may apply to any therapy that employs stimulation pulses of electrical or other form of energy.

FIG. 1 illustrates an embodiment of a neurostimulation system 100. System 100 includes electrodes 106, a stimulation device 104, and a programming device 102. Electrodes 106 are configured to be placed on or near one or more neural targets in a patient. Stimulation device 104 is configured to be electrically connected to electrodes 106 and deliver neurostimulation energy, such as in the form of electrical pulses, to the one or more neural targets though electrodes 106. The delivery of the neurostimulation is controlled by using a plurality of stimulation parameters, such as stimulation parameters specifying a pattern of the electrical pulses and a selection of electrodes through which each of the electrical pulses is delivered. In various embodiments, at least some parameters of the plurality of stimulation parameters are programmable by a user, such as a physician or other caregiver who treats the patient using system 100. Programming device 102 provides the user with accessibility to the user-programmable parameters. In various embodiments, programming device 102 is configured to be communicatively coupled to stimulation device via a wired or wireless link.

In various embodiments, programming device 102 includes a user interface that allows the user to set and/or adjust values of the user-programmable parameters by creating and/or editing graphical representations of various waveforms. Such waveforms may include, for example, the waveform of a pattern of neurostimulation pulses to be delivered to the patient as well as waveform building blocks that can be used in the pattern of neurostimulation pulses. Examples of such waveform building blocks include pulses, bursts each including a group of the pulses, trains each including a group of the bursts, and sequences each including a group of the pulses, bursts, and trains, as further discussed below. In various embodiments, programming device 102 allows the user to edit existing waveform building blocks, create new waveform building blocks, import waveform building blocks created by other users, and/or export waveform building blocks to be used by other users. The user may also be allowed to define an electrode selection specific to each waveform building block. In the illustrated embodiment, the user interface includes a user interface 110. In various embodiments, user interface 110 may include a GUI or any other type of user interface accommodating various functions including waveform composition as discussed in this document.

Figure 2:
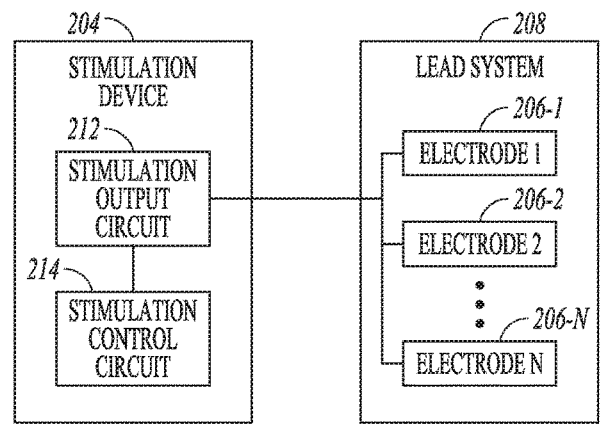
FIG. 2 illustrates an embodiment of a stimulation device and a lead system, such as may be implemented in the neurostimulation system of FIG. 1.

FIG. 2 illustrates an embodiment of a stimulation device 204 and a lead system 208, such as may be implemented in neurostimulation system 100. Stimulation device 204 represents an embodiment of stimulation device 104 and includes a stimulation output circuit 212 and a stimulation control circuit 214. Stimulation output circuit 212 produces and delivers neurostimulation pulses. Stimulation control circuit 214 controls the delivery of the neurostimulation pulses using the plurality of stimulation parameters, which specifies a pattern of the neurostimulation pulses. Lead system 208 includes one or more leads each configured to be electrically connected to stimulation device 204 and a plurality of electrodes 206 distributed in the one or more leads.

The plurality of electrodes 206 includes electrode 206-1, electrode 206-2, . . . electrode 206-N, each a single electrically conductive contact providing for an electrical interface between stimulation output circuit 212 and tissue of the patient, where N≥2. The neurostimulation pulses are each delivered from stimulation output circuit 212 through a set of electrodes selected from electrodes 206.

In various embodiments, the number of leads and the number of electrodes on each lead depend on, for example, the distribution of target(s) of the neurostimulation and the need for controlling the distribution of electric field at each target. In one embodiment, lead system 208 includes 2 leads each having 8 electrodes.

Figure 3:
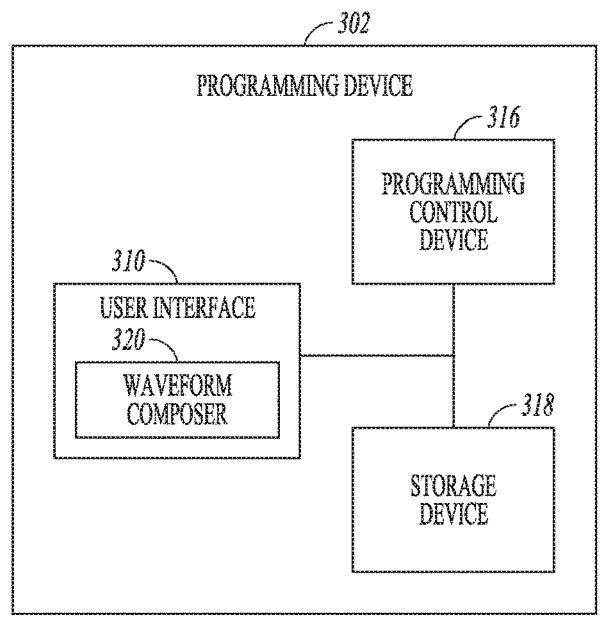
FIG. 3 illustrates an embodiment of a programming device, such as may be implemented in the neurostimulation system of FIG. 1.

FIG. 3 illustrates an embodiment of a programming device 302, such as may be implemented in neurostimulation system 100. Programming device 302 represents an embodiment of programming device 102 and includes a storage device 318, a programming control circuit 316, and a user interface 310. Storage device 318 stores a plurality of waveform building blocks. Programming control circuit 316 generates the plurality of stimulation parameters that controls the delivery of the neurostimulation pulses according to the pattern of the neurostimulation pulses. User interface 310 represents an embodiment of user interface 110 and allows the user to compose the waveform building blocks and compose the pattern of the neurostimulation pulses using one or more waveform building blocks selected from the plurality of waveform building blocks.

In various embodiments, user interface 310 includes a waveform composer 320 that allows the user to manage the waveform building blocks, including creating and importing waveform building blocks to be added to the waveform building blocks stored in storage device 318, exporting waveform building blocks selected from the waveform building blocks stored in storage device 318, and editing each of the waveform building blocks. In various embodiments, user interface 310 includes a GUI that allows for graphical editing of each of the waveform building blocks. In various embodiments, waveform composer 320 allows the user to compose the pattern of neurostimulation pulses to be delivering to the patent using stimulation device 104 using waveform building blocks such as pulses, bursts each including a group of the pulses, trains each including a group of the bursts, and/or sequences each including a group of the pulses, bursts, and trains. In various embodiments, waveform composer 320 allows the user to create each waveform building block using one or more waveform building blocks stored in storage device 318 as templates. In various embodiments, waveform composer 320 allows each newly created waveform building block to be saved as additional waveform building block stored in storage device 318.

In one embodiment, user interface 310 includes a touchscreen. In various embodiments, user interface 310 includes any type of presentation device, such as interactive or non-interactive screens, and any type of user input devices that allow the user to edit the waveforms or building blocks and schedule the programs, such as touchscreen, keyboard, keypad, touchpad, trackball, joystick, and mouse. In various embodiments, circuits of neurostimulation 100, including its various embodiments discussed in this document, may be implemented using a combination of hardware and software. For example, the circuit of user interface 100, stimulation control circuit 214, and programming control circuit 316, including their various embodiments discussed in this document, may be implemented using an application-specific circuit constructed to perform one or more particular functions or a general-purpose circuit programmed to perform such function(s). Such a general-purpose circuit includes, but is not limited to, a microprocessor or a portion thereof, a microcontroller or portions thereof, and a programmable logic circuit or a portion thereof.

Figure 4:
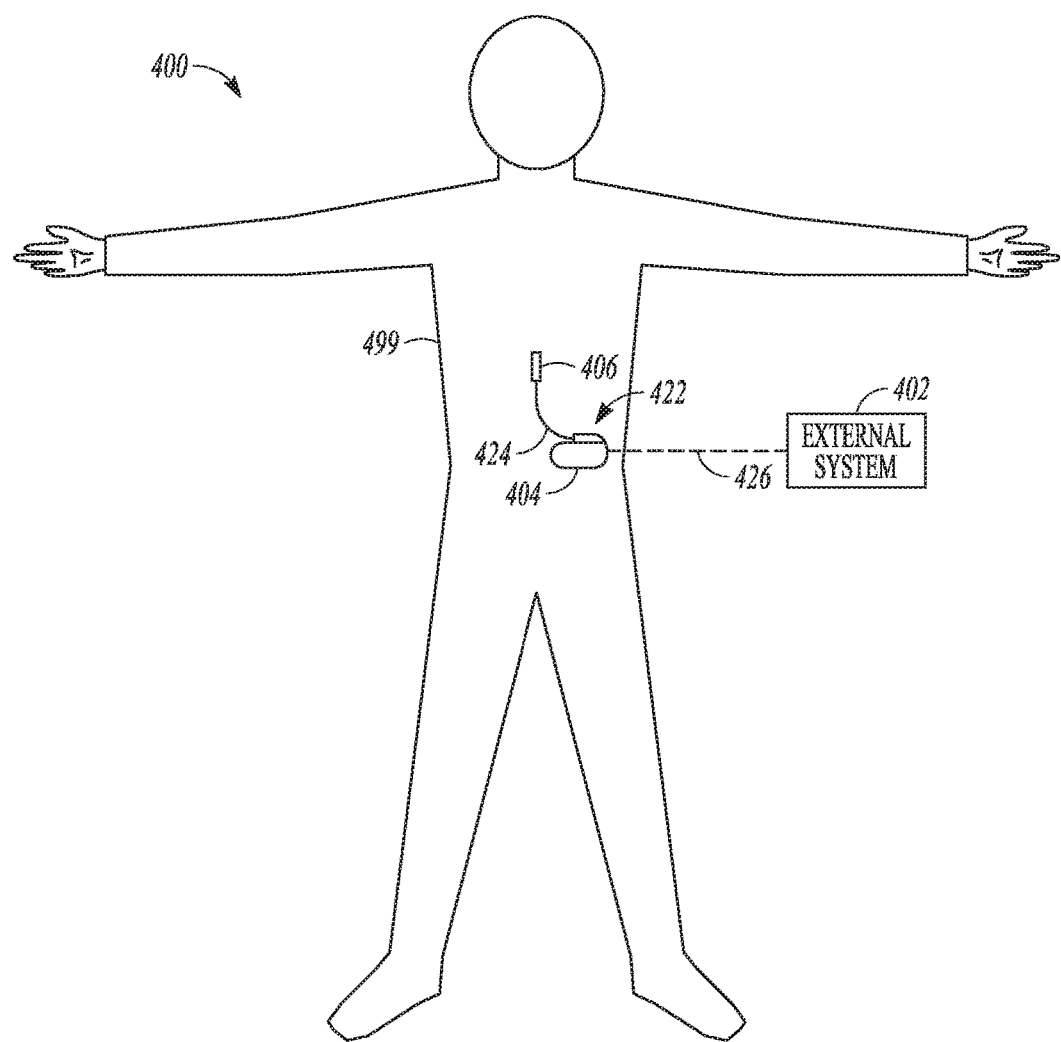
FIG. 4 illustrates an implantable neurostimulation system and portions of an environment in which the system may be used.

FIG. 4 illustrates an implantable neurostimulation system 400 and portions of an environment in which system 400 may be used. System 400 includes an implantable system 422, an external system 402, and a telemetry link 426 providing for wireless communication between implantable system 422 and external system 402. Implantable system 422 is illustrated in FIG. 4 as being implanted in the patient's body 499.

Implantable system 422 includes an implantable stimulator (also referred to as an implantable pulse generator, or IPG) 404, a lead system 424, and electrodes 406, which represent an embodiment of stimulation device 204, lead system 208, and electrodes 206, respectively. External system 402 represents an embodiment of programming device 302. In various embodiments, external system 402 includes one or more external (non-implantable) devices each allowing the user and/or the patient to communicate with implantable system 422. In some embodiments, external 402 includes a programming device intended for the user to initialize and adjust settings for implantable stimulator 404 and a remote control device intended for use by the patient. For example, the remote control device may allow the patient to turn implantable stimulator 404 on and off and/or adjust certain patient-programmable parameters of the plurality of stimulation parameters.

The sizes and sharps of the elements of implantable system 422 and their location in body 499 are illustrated by way of example and not by way of restriction. An implantable system is discussed as a specific application of the programming according to various embodiments of the present subject matter. In various embodiments, the present subject matter may be applied in programming any type of stimulation device that uses electrical pulses as stimuli, regarding less of stimulation targets in the patient's body and whether the stimulation device is implantable.

Figure 5:
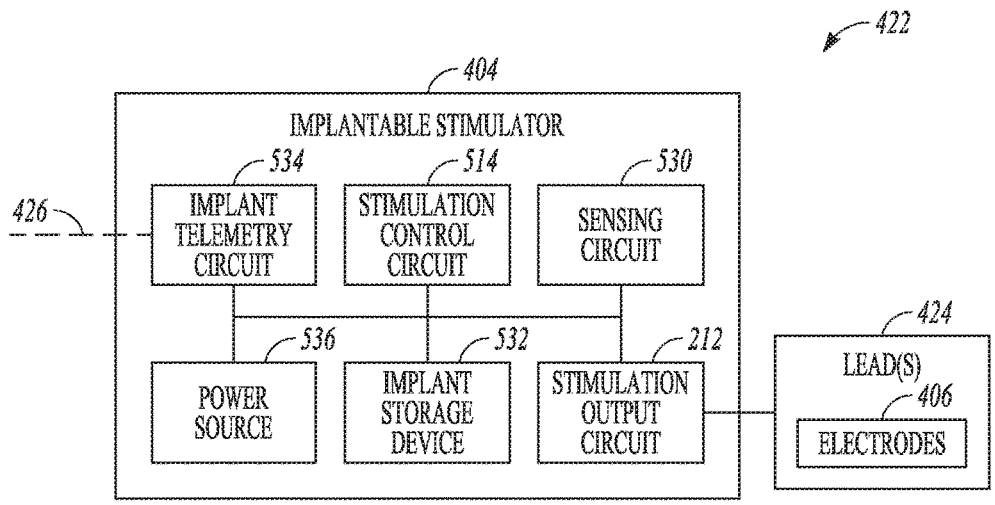
FIG. 5 illustrates an embodiment of an implantable stimulator and one or more leads of an implantable neurostimulation system, such as the implantable system of FIG. 4.

FIG. 5 illustrates an embodiment of implantable stimulator 404 and one or more leads 424 of an implantable neurostimulation system, such as implantable system 422. Implantable stimulator 404 may include a sensing circuit 530 that is optional and required only when the stimulator has a sensing capability, stimulation output circuit 212, a stimulation control circuit 514, an implant storage device 532, an implant telemetry circuit 534, and a power source 536. Sensing circuit 530, when included and needed, senses one or more physiological signals for purposes of patient monitoring and/or feedback control of the neurostimulation. Examples of the one or more physiological signals includes neural and other signals each indicative of a condition of the patient that is treated by the neurostimulation and/or a response of the patient to the delivery of the neurostimulation. Stimulation output circuit 212 is electrically connected to electrodes 406 through lead 424, and delivers each of the neurostimulation pulses through a set of electrodes selected from electrodes 406. Stimulation control circuit 514 represents an embodiment of stimulation control circuit 214 and controls the delivery of the neurostimulation pulses using the plurality of stimulation parameters specifying the pattern of the neurostimulation pulses. In one embodiment, stimulation control circuit 514 controls the delivery of the neurostimulation pulses using the one or more sensed physiological signals. Implant telemetry circuit 534 provides implantable stimulator 404 with wireless communication with another device such as a device of external system 402, including receiving values of the plurality of stimulation parameters from external system 402. Implant storage device 532 stores values of the plurality of stimulation parameters. Power source 536 provides implantable stimulator 404 with energy for its operation. In one embodiment, power source 536 includes a battery. In one embodiment, power source 536 includes a rechargeable battery and a battery charging circuit for charging the rechargeable battery. Implant telemetry circuit 534 may also function as a power receiver that receives power transmitted from external system 402 through an inductive couple.

In various embodiments, sensing circuit 530 (if included), stimulation output circuit 212, stimulation control circuit 514, implant telemetry circuit 534, implant storage device 532, and power source 536 are encapsulated in a hermetically sealed implantable housing. In various embodiments, lead(s) 424 are implanted such that electrodes 406 are places on and/or around one or more targets to which the neurostimulation pulses are to be delivered, while implantable stimulator 404 is subcutaneously implanted and connected to lead(s) 424 at the time of implantation.

Figure 6:
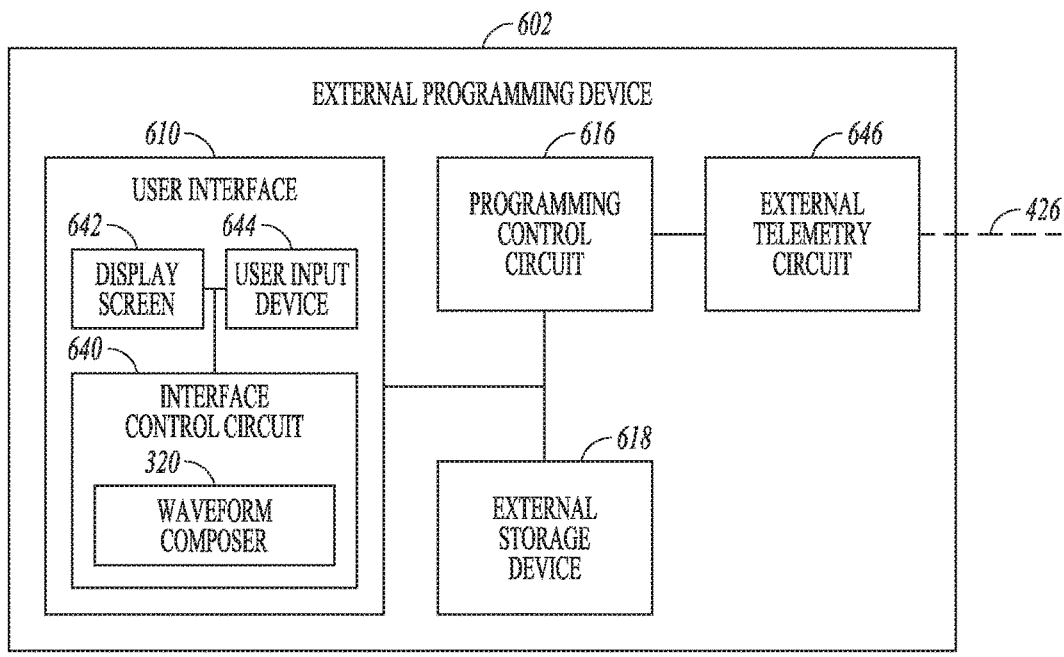
FIG. 6 illustrates an embodiment of an external programming device of an implantable neurostimulation system, such as the external system of FIG. 4.

FIG. 6 illustrates an embodiment of an external programming device 602 of an implantable neurostimulation system, such as external system 402. External programming device 602 represents an embodiment of programming device 302, and includes an external telemetry circuit 646, an external storage device 618, a programming control circuit 616, and a user interface 610.

External telemetry circuit 646 provides external programming device 602 with wireless communication with another device such as implantable stimulator 404 via telemetry link 426, including transmitting the plurality of stimulation parameters to implantable stimulator 404. In one embodiment, external telemetry circuit 646 also transmits power to implantable stimulator 404 through the inductive couple.

External storage device 618 stores a plurality of waveform building blocks each selectable for use as a portion of the pattern of the neurostimulation pulses. In various embodiments, each waveform building block of the plurality of waveform building blocks includes one or more pulses of the neurostimulation pulses, and may include one or more other waveform building blocks of the plurality of waveform building blocks. Examples of such waveforms include pulses, bursts each including a group of the pulses, trains each including a group of the bursts, and sequences each including a group of the pulses, bursts, and trains. External storage device 618 also stores a plurality of stimulation fields. Each waveform building block of the plurality of waveform building blocks is associated with one or more fields of the plurality of stimulation fields. Each field of the plurality of stimulation fields is defined by one or more electrodes of the plurality of electrodes through which a pulse of the neurostimulation pulses is delivered and a current distribution of the pulse over the one or more electrodes.

Programming control circuit 616 represents an embodiment of programming control circuit 316 and generates the plurality of stimulation parameters, which is to be transmitted to implantable stimulator 404, according to the pattern of the neurostimulation pulses. The pattern is defined using one or more waveform building blocks selected from the plurality of waveform building blocks stored in external storage device 618. In various embodiment, programming control circuit 616 checks values of the plurality of stimulation parameters against safety rules to limit these values within constraints of the safety rules. In one embodiment, the safety rules are heuristic rules.

User interface 610 represents an embodiment of user interface 310 and allows the user to define the pattern of neurostimulation pulses and perform various other monitoring and programming tasks. In one embodiment, user interface 610 includes a GUI. User interface 610 includes a display screen 642, a user input device 644, and an interface control circuit 640. Display screen 642 may include any type of interactive or non-interactive screens, and user input device 644 may include any type of user input devices that supports the various functions discussed in this document, such as touchscreen, keyboard, keypad, touchpad, trackball, joystick, and mouse. In one embodiment, user interface 610 includes a GUI that has an interactive screen for displaying a graphical representation of a waveform building block and allows the user to adjust the waveform building block by graphically editing the waveform building block. User interface 610 may also allow the user to perform any other functions discussed in this document where graphical editing is suitable as may be appreciated by those skilled in the art.

Interface control circuit 640 controls the operation of user interface 610 including responding to various inputs received by user input device 644 and defining the one or more stimulation waveforms. Interface control circuit 640 includes waveform composer 320.

In various embodiments, external programming device 602 has operation modes including a composition mode and a real-time programming mode. Under the composition mode (also known as the pulse pattern composition mode), User interface 610 is activated, while programming control circuit 616 is inactivated. Programming control circuit 616 does not dynamically updates values of the plurality of stimulation parameters in response to any change in the one or more stimulation waveforms. Under the real-time programming mode, both user interface 610 and programming control circuit 616 are activated. Programming control circuit 616 dynamically updates values of the plurality of stimulation parameters in response to changes in the set of one or more stimulation waveforms, and transmits the plurality of stimulation parameters with the updated values to implantable stimulator 404.

Figure 7:
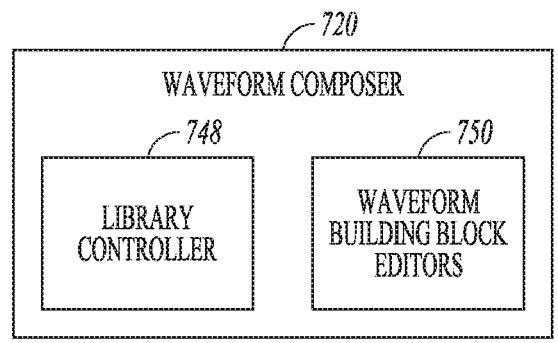
FIG. 7 illustrates an embodiment of a waveform composer of an external programming device, such as the external programming device of FIG. 6.

FIG. 7 illustrates an embodiment of a waveform composer 720, which represents an embodiment of waveform composer 320. Waveform composer 720 allows for composition of one of more waveform building blocks of the plurality of waveform building blocks stored in external storage device 618 and composition of the pattern of the neurostimulation pulses using one of more stimulation building blocks selected from the plurality of waveform building blocks stored in external storage device 618. In the illustrated embodiment, waveform composer includes a library controller 748 and a plurality of waveform building block editors 750. Library controller 748 displays a library management area on display screen 642. The displayed library management area allows the user to manage the waveform building blocks stored in external storage device 618. Waveform building block editors 750 each display a composition area for a type of the waveform building blocks of a plurality of types of the waveform building blocks on display screen 642. The displayed composition area allows the user to compose each waveform building block of the type of the waveform building blocks.

In various embodiments, waveform building block editors 750 each display a composition area for a type of the waveform building blocks of the plurality of types of the waveform building blocks on display screen 642 in response to a user selection of the type of the waveform building blocks. The displayed composition area allows the user to compose a waveform building block of the type of the waveform building blocks. The composition of the waveform building block includes editing a waveform building block selected from the waveform building blocks stored in external storage device 618 or creating a new waveform building block to be added to the waveform building blocks stored in external storage device 618.

In various embodiments, each type of the plurality of types of the waveform building blocks represents a level of a plurality of levels of the waveform building blocks. A waveform building block of each level may include one or more waveform building blocks of one or more lower levels. In various embodiments, the plurality of types of the waveform building blocks may include, but is not limited to, pulses (e.g., each having a time scale of milliseconds), bursts (e.g., each having a time scale of milliseconds to seconds) each including a group of the pulses, trains e.g., each having a time scale of milliseconds to minutes) each including a group of the bursts, and sequences (e.g., each having a time scale of minutes to weeks) each including a group of the pulses, bursts, and trains. Pauses (each being a time interval during which no pulse is to be delivered) may each be placed between two of the waveform building blocks. The sequences may each be composed for a specific therapy. The levels in the order from the lowest to the highest: pulse, burst, train, and sequence;

In various embodiments, waveform composer 720 allows each of library controller 748 and editors of the plurality of waveform building block editors 750 to be selected by the user for access. In one embodiment, waveform composer 720 displays on display screen 642 tags each associated with one of the library controller and the editors of the plurality of waveform building block editors, and allows the user to select a tag from the displayed tags. In various embodiments, waveform composer 720 allows the delivery of the neurostimulation pulses to be turned on and off, such that the user can decide whether to suspend the delivery of the neurostimulation pulses during the composition of waveform building blocks and/or composition of the pattern of the neurostimulation pulses.

Figure 8:
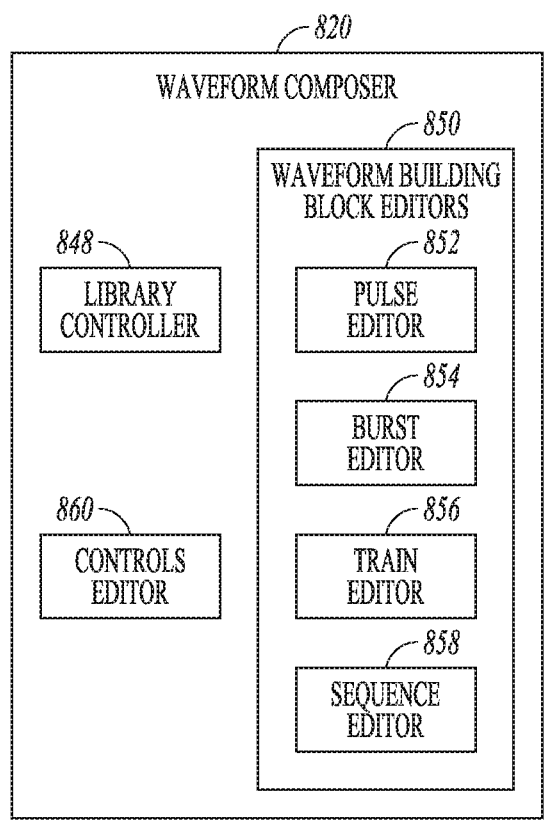
FIG. 8 illustrates another embodiment of the waveform composer of an external programming device, such as the external programming device of FIG. 6.

FIG. 8 illustrates an embodiment of a waveform composer 820, which represent an embodiment of waveform composer 720. Waveform composer 820 includes a library controller 848, a plurality of waveform building block editors 850, and a controls editor 860.

Library controller 848 represents an embodiment of library controller 748 and displays a library management area on display screen 642 in response to a user selection for access to the library controller. FIG. 9 illustrates an embodiment of a screen (such as display screen 642) displaying such a library management area. The library management area allows for management of the waveform building blocks stored in external storage device 618. The waveform building blocks are each displayed with a reference number, a kind (type), a name, a preview, and dependency (on one or more other stored waveform building blocks), and are each selectable for editing by a corresponding editor of the plurality of waveform building block editors 850. In the illustrated embodiment, the waveform building blocks stored in storage device 618 are each belong to a library of a plurality of libraries including, by way of example but not by way of restriction, a default library including standard waveform building blocks provided by the manufacturer, a programmer library including waveform building blocks specifically selected for an individual patient (i.e., stored specifically for the patient), and a patient library including waveform building blocks currently used as part of the pattern of the neurostimulation pulses for the patient.

Waveform building block editors 850 represents an embodiment of waveform building block editors 750, and includes an editor for each type of the plurality of types of waveform building blocks. In the illustrated embodiment, waveform building block editors 850 include a pulse editor 852, a burst editor 854, a train editor 856, and a sequence editor 858.

Figure 10:
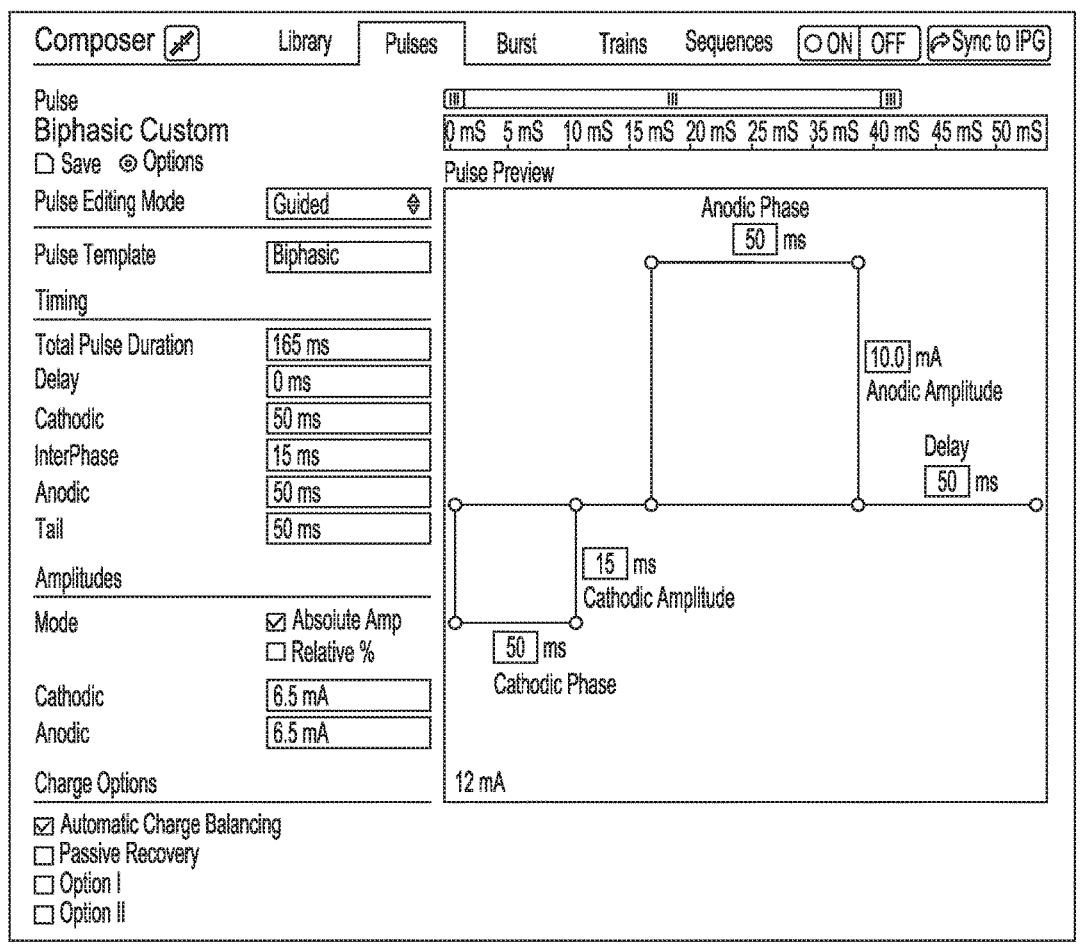
FIG. 10 illustrates an embodiment of the screen displaying a pulse composition area.

Pulse editor 852 displays a pulse composition area on display screen 642 in response to a user selection for access to the pulse editor. The pulse composition area allows the user to compose a pulse of the waveform building blocks. FIG. 10 illustrates an embodiment of a screen (such as display screen 642) displaying such a pulse composition area. The pulse composition area allows the user to edit a pulse selected from the waveform building blocks stored in external storage device 618 and to create anew pulse to be added to the waveform building blocks stored in external storage device 618. The pulse composition area displays a graphical representation of the pulse being edited or created and a slider for shifting, expanding, or contracting a timeline of the graphical representation of the pulse. The pulse composition area allows the user to select a pulse editing mode from a plurality of pulse editing modes, such as by displaying a pull down menu listing the plurality of pulse editing modes as illustrated. Examples of the pulse editing modes include, but are not limited to, a guided mode, a free form mode, and a draw mode. Under the guided mode, values of parameters defining the pulse are displayed, and the user is allowed to edit the pulse by adjusting the displayed values of the parameters. Under the free form mode, the user is allowed to edit the pulse by graphically modifying the displayed graphical representation of the pulse. Under the draw mode, the user is allowed to sketch a waveform for the pulse. In response to a selection of automatic charge balancing by the user, pulse editor 842 can automatically modify the pulse for charge balancing.

Figure 11:
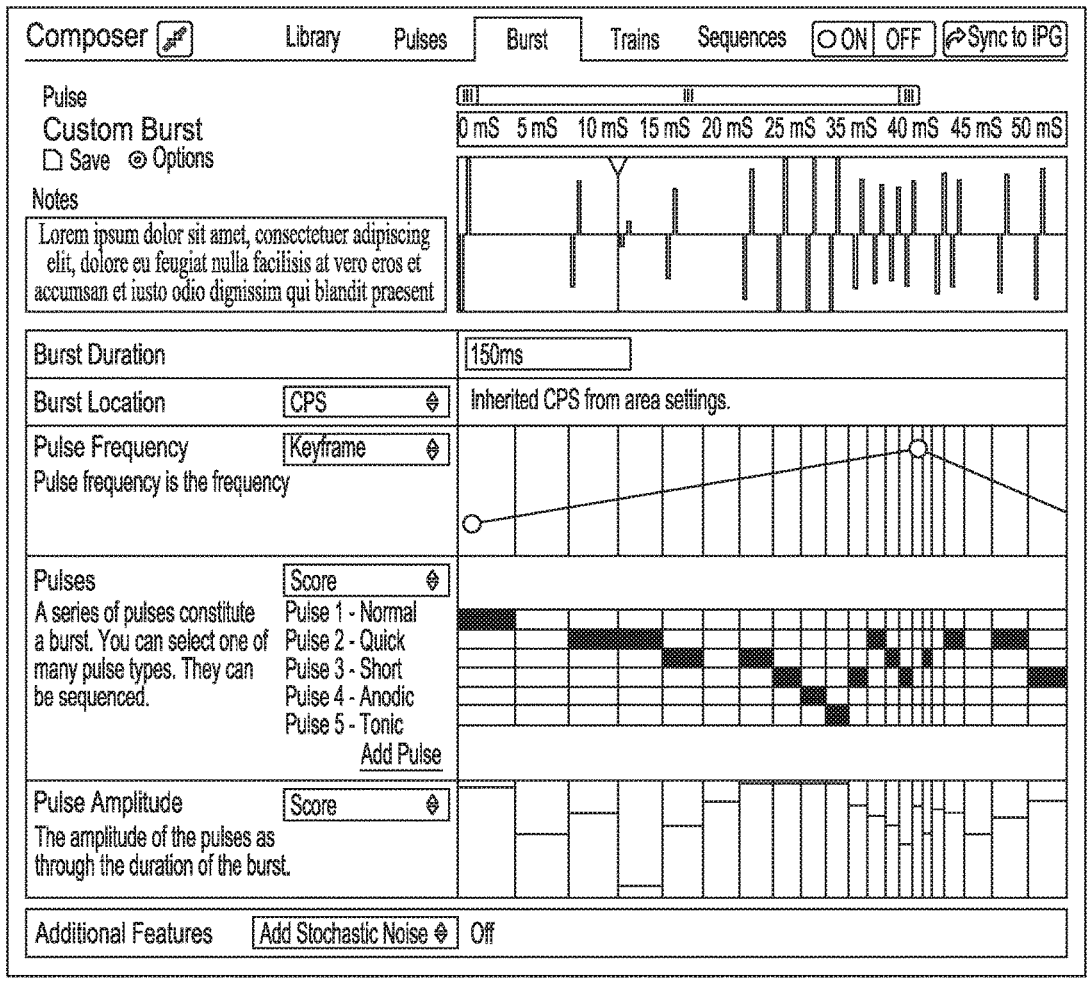
FIG. 11 illustrates an embodiment of the screen displaying a burst composition area.

Burst editor 854 displays a burst composition area on display screen 642 in response to a user selection for access to the burst editor. The burst composition area allows the user to compose a burst of the waveform building blocks. FIG. 11 illustrates an embodiment of a screen (such as display screen 642) displaying such a burst composition area. The burst composition area allows the user to edit a burst selected from the waveform building blocks stored in external storage device 618 or to create a new burst to be added to the waveform building blocks stored in external storage device 618. The burst composition area displays a preview of a waveform of the burst and allows for saving of modified waveform of the burst. The burst composition area allows the user to select options for editing each of the characteristics of the burst, such as duration, location (location in the body of the patient to which the burst is applied, i.e., electrode configuration), pulse frequency, pulse type, and pulse amplitude.

Figure 12:
FIG. 12 illustrates an embodiment of the screen displaying a train composition area.

Train editor 846 displays a train composition area on display screen 642 in response to a user selection for access to the train editor. The train composition area allows the user to compose a train of the waveform building blocks. FIG. 12 illustrates an embodiment of a screen (such as display screen 642) displaying such a train composition area. The train composition area allows the user to edit a train selected from the waveform building blocks stored in external storage device 618 or to create a new train to be added to the waveform building blocks stored in external storage device 618. The train composition area displays a preview of a waveform of the train and allows for saving of modified waveform of the train. The train composition area allows the user to select options for editing each of the characteristics of the train, such as duration, burst location, burst frequency, train configuration, and burst amplitude.

Figure 13:
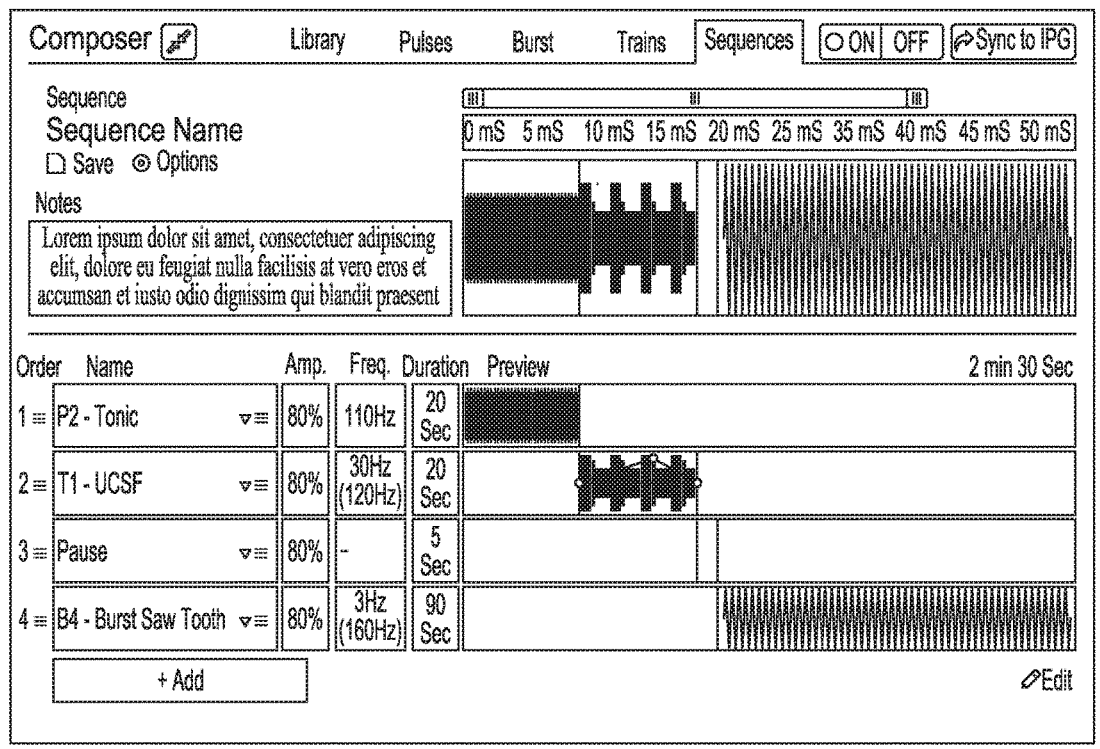
FIG. 13 illustrates an embodiment of the screen displaying a sequence composition area.

Sequence editor 848 displays a sequence composition area on display screen 642 in response to a user selection for access to the sequence editor. The sequence composition area allows the user to compose a sequence of the waveform building blocks. FIG. 13 illustrates an embodiment of a screen (such as display screen 642) displaying such a sequence composition area. The sequence composition area allows the user to edit a sequence selected from the waveform building blocks stored in external storage device 618 or to create a new sequence to be added to the waveform building blocks stored in external storage device 618. The sequence composition area displays a preview of a waveform of the sequence and allows for saving of modified waveform of the sequence. The sequence composition area allows for selection of a sequence editing option from a plurality of sequence editing modes, allows for addition and deletion of waveform building blocks (sequence components) in the sequence, and allows for simple editing of the waveform building blocks within the sequence composition area.

Figure 14:
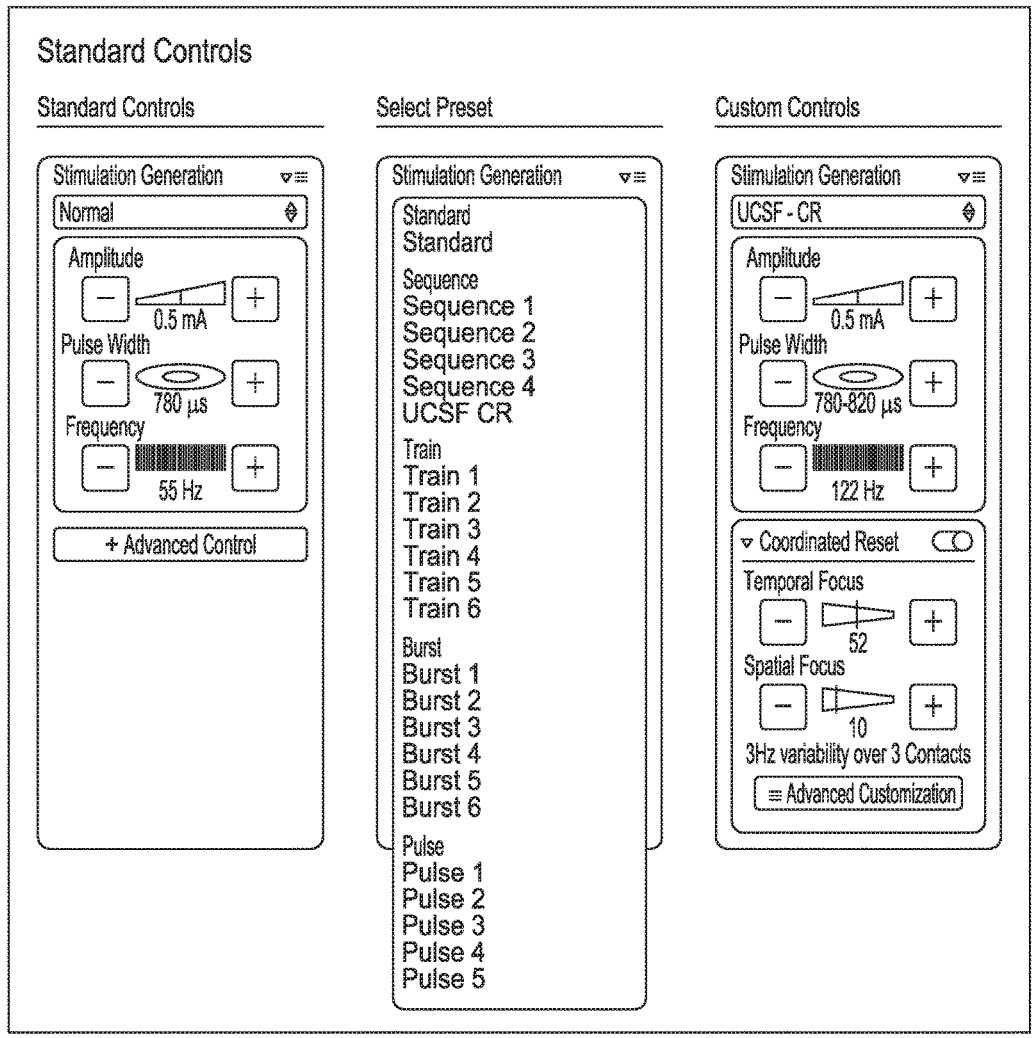
FIG. 14 illustrates an embodiment of the screen displaying a controls area.

Controls editor 860 displays a controls area on display screen 642 in response to a user command. The controls area allows the user to edit pulse parameters used for a waveform building block. FIG. 14 illustrates an embodiment of a screen (such as display screen 642) displaying a controls area. The control area allows the user to select a waveform building block and applies various pulse parameter to the selected waveform building block. The pulse parameters include pulse amplitude, pulse width, and pulse frequency. The control area allows the user to select advanced control including advanced editing options listed in a pull down menu, select coordinated reset for applying the edited pulse parameters (custom controls) to the selected waveform building block, and select how a pulse parameter of the pulse parameters is defined for the selected waveform building block.

Figure 15:
FIG. 15 illustrates an embodiment of the screen displaying controls for pulse amplitude.

FIG. 15 illustrates an embodiment of the control area for editing the pulse amplitude. Available editing options for specifying the pulse amplitude include "Fixed" (constant pulse amplitude for the waveform building block, adjustable by a slider displayed on the control area), "Holdframe" (specified by one or more values and a holding duration for each value of the one or more values), "Keyframe" (specified by an envelope function defined for the waveform building block), and "Score" (specified by a number, i.e., score, for each segment of one or more time segments of the waveform building block).

Figure 16:
FIG. 16 illustrates an embodiment of the screen displaying controls for pulse type.

FIG. 16 illustrates an embodiment of the control are displaying controls for pulse type. Available editing options for specifying the pulse type include "Constant" (constant pulse type for the waveform building block), "Score" (specified by a number, i.e., score, for each segment of one or more time segments of the waveform building block), and "Distorted" (some type of variance to a pulse parameter specified, such as slowly varying pulse amplitude, pulse width, or shape).

In various embodiments, waveform composer 820 displays the library management area, the pulse composition area, the burst composition area, the train composition area, the sequence composition area, and the controls area on display screen 642 one at a time according to a selection made by the user. This allows the user to focus on one task (area) at a time without distraction, while being able to switch to another area directly from the displayed area.

Figure 17:
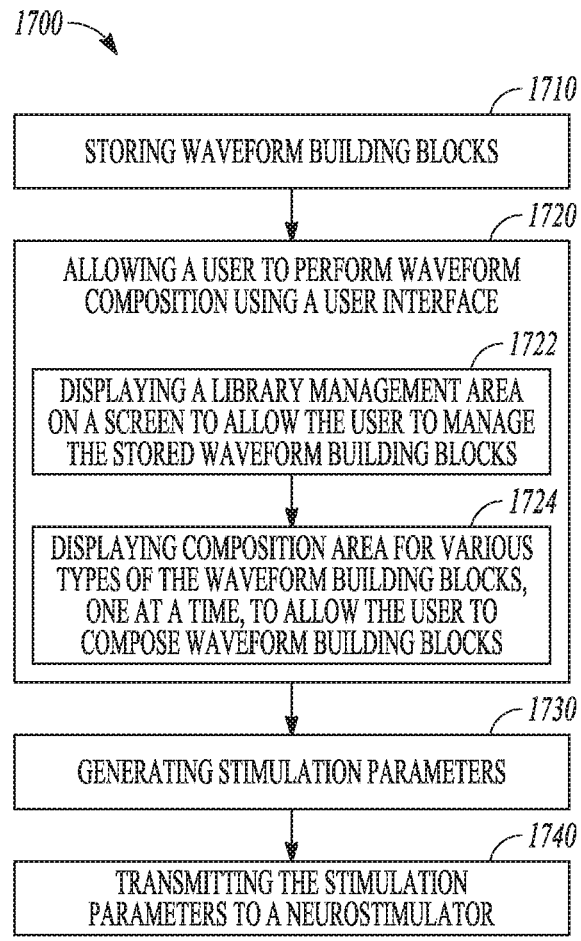
FIG. 17 illustrates an embodiment of a method for operating a programming device for neurostimulation.

FIG. 17 illustrates an embodiment of a method 1700 for operating a programming device for neurostimulation. In one embodiment, method 1700 is applied in system 100, including various embodiments of its elements discussed in this document.

At 1710, waveform building blocks are stored in a storage device of the programming device. Examples of the waveform building blocks include, but are not limited to, the pulses, bursts, trains, and sequences as discussed above in this document.

At 1720, a user is allowed to perform waveform composition using a user interface of the programming device. The waveform composition includes composition of one of more waveform building blocks and composition of a pattern of the neurostimulation pulses using one of more waveform building blocks selected from the waveform building blocks stored in the storage device. At 1722, a library management area is displayed on a screen of the user interface. The displayed library management area allows the user to manage the stored waveform building blocks using a user input device of the user interface. In one embodiment, the waveform building blocks displayed in the library management area are each selectable for editing. At 1724, a composition area for a type of the waveform building blocks of a plurality of types of the waveform building blocks is displayed on the screen. The displayed composition area allows the user to compose a building block of the type of the waveform building blocks using the user input device. In one embodiment, a controls area is displayed on the screen in response to a user command. The controls area allows the user to edit pulse parameters for a waveform building block selected from the waveform building blocks. In various embodiments, the composition area is displayed to allow the user to edit a waveform building block selected from the stored waveform building blocks and to allow the user to create a new building block to be added to the stored waveform building blocks. In various embodiments, performing a waveform composition includes receiving a user selection and displaying the library management area or the composition area, one at a time, according to the user selection. The composition area corresponds to the type of the waveform building blocks selected from the plurality of types of the waveform building blocks according to the user selection. In various embodiments, the user is allowed to import a waveform building block to be added to the stored waveform building blocks and to export a waveform building block selected from the stored waveform building blocks.

At 1730, a plurality of stimulation parameters controlling delivery of neurostimulation pulses from the neurostimulator is generated according to a pattern of the neurostimulation pulses. At 1740, the plurality of stimulation parameters is transmitted to a neurostimulator to control delivery of neurostimulation pulses according to the pattern of the neurostimulation pulses.

Figure 18:
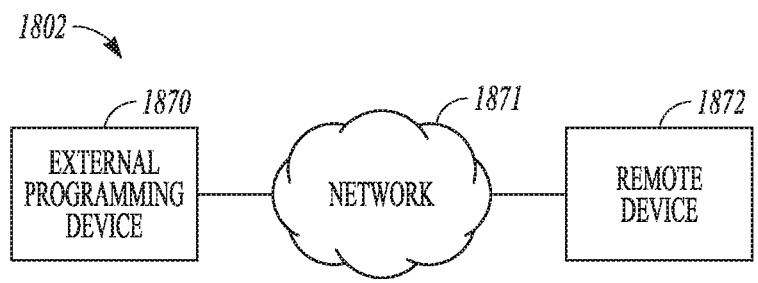
FIG. 18 illustrates an embodiment of an external system, such as may be implemented in the implantable neurostimulation system of FIG. 4.

In various embodiments, external system 402 may include one or more devices. FIG. 18 illustrates an embodiment of an external system 1802, such as may be implemented in implantable neurostimulation system 400. External system 1802 represents an embodiment of external system 402. In the illustrated embodiment, external system 1802 includes an external programming device 1870, a remote device 1872, and a network 1871 coupled between external programming device 1870 and remote device 1872. In various embodiments, external programming device 1870 and remote device 1872 are communicatively coupled to each other via a wired or wireless communication link. This allows, for example, stimulation waveforms or waveform building blocks to be composed in a device other than the programming device that directly transmits the stimulation parameters to the stimulation device. In other embodiments, external programming device 1870 and remote device 1872 may be physically integrated into a single device such as external programming device 602. Thus, the various user interface features discussed in this document, such as with reference to FIGS. 9-16, 21-30, and 32-38 may be implemented in external system 402, external system 1802, or other external systems capable of performing waveform composition, stimulation adjustment, and device programming functions discussed in this document.

In one embodiment, external programming device 1870 may be configured for use by users such as clinicians and/or medical technicians who program stimulation devices for patients, while remote device may be configured for use by researchers and/or clinicians who composes the stimulation waveforms. In other words, remote device 1872 may be used to develop neurostimulation patterns, and external programming device 1870 may be used to apply the neurostimulation patterns to patients, with limited adjustment or customization for each patient. This allows users with different levels of expertise and/or tasks to focus on their tasks without being distracted or overwhelmed by the amount of programmable variables that can be controlled by external system 1802. In various embodiments, remote device 1872 may be a computer programmed to allow for development of the neurostimulation patterns. While remote device 1872 is shown in FIG. 18 for illustrated purposes, external system 1802 may include one or more remote devices that are capable of waveform composition as discussed in this document. This allows multiple users to participate in the development of settings for a neurostimulation therapy.

Figure 19:
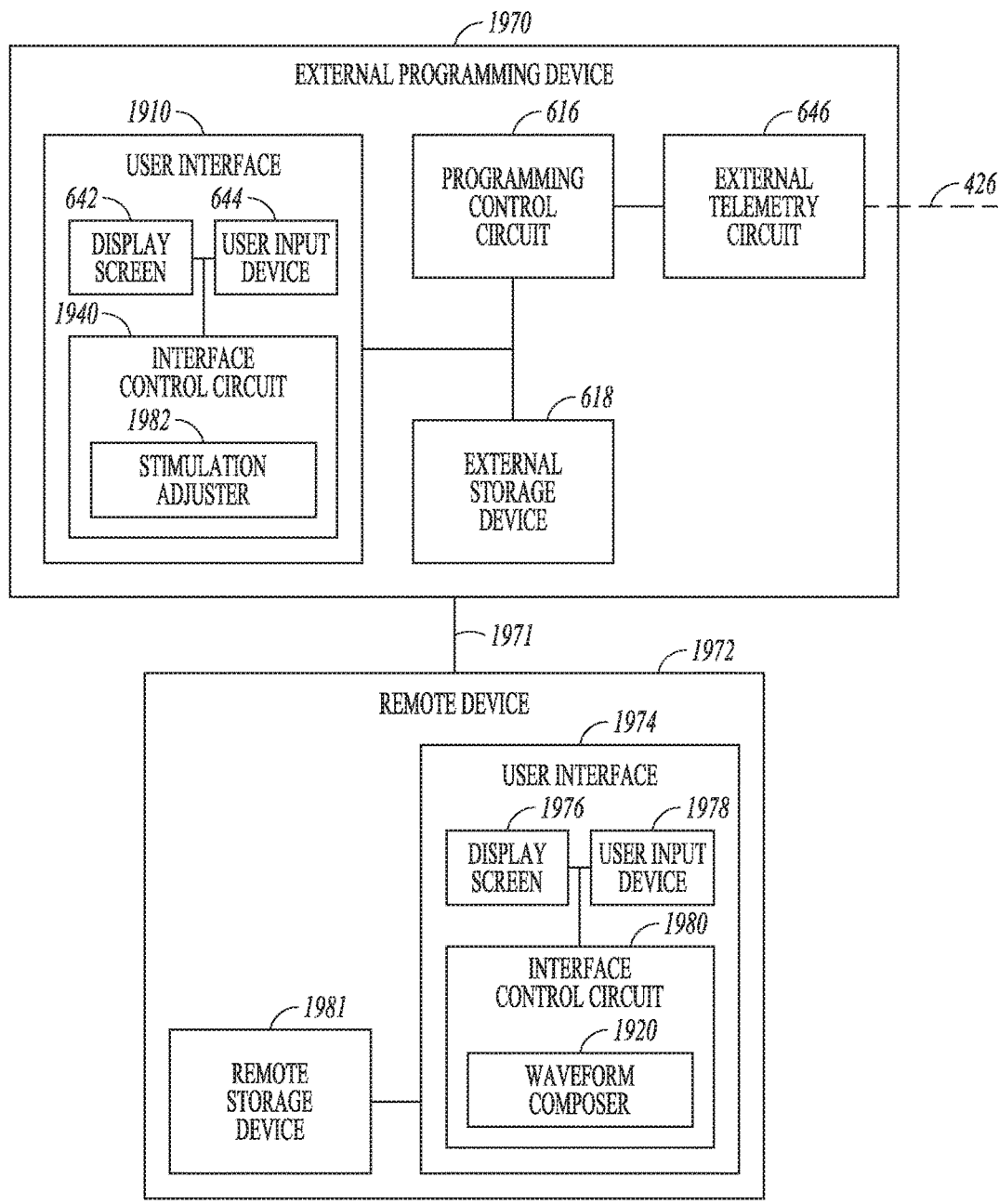
FIG. 19 illustrates an embodiment of an external programming device and a remote device of an external system, such as the external system of FIG. 18.

FIG. 19 illustrates an embodiment of an external programming device 1970 and a remote device 1972 of an external system, such as external system 1802. External programming device 1902 includes external telemetry circuit 646, external storage device 618, programming control circuit 616, and a user interface 1910. Remote device 1972 includes a user interface 1974 and a remote storage device 1981. External programming device 1902 and remote device 1972 are communicatively coupled to each other via a wired or wireless communication link 1971. In one embodiment, communication link 1971 includes portions of a network.

External telemetry circuit 646 provides external programming device 1970 with wireless communication with another device such as implantable stimulator 404 via telemetry link 426, including transmitting the plurality of stimulation parameters to implantable stimulator 404. In one embodiment, external telemetry circuit 646 also transmits power to implantable stimulator 404 through the inductive couple.

External storage device 618 stores a plurality of waveform building blocks each selectable for use as a portion of the pattern of the neurostimulation pulses. In various embodiments, the plurality of waveform building blocks include waveform building blocks imported from remote device 1972 and/or any other source where waveform building blocks may be composed. In various embodiments, the plurality of waveform building blocks may also include waveform building blocks created and/or edited by the user using external programming device 1970. In various embodiments, each waveform building block of the plurality of waveform building blocks includes one or more pulses of the neurostimulation pulses, and may include one or more other waveform building blocks of the plurality of waveform building blocks. Examples of such waveforms include pulses, bursts each including a group of the pulses, trains each including a group of the bursts, and sequences each including a group of the pulses, bursts, and trains. External storage device 618 also stores a plurality of stimulation fields. Each waveform building block of the plurality of waveform building blocks is associated with one or more fields of the plurality of stimulation fields. Each field of the plurality of stimulation fields is defined by one or more electrodes of the plurality of electrodes through which a pulse of the neurostimulation pulses is delivered and a current distribution of the pulse over the one or more electrodes.

Programming control circuit 616 represents an embodiment of programming control circuit 316 and generates the plurality of stimulation parameters, which is to be transmitted to implantable stimulator 404, according to the pattern of the neurostimulation pulses. The pattern is defined using one or more waveform building blocks selected from the plurality of waveform building blocks stored in external storage device 618. In various embodiment, programming control circuit 616 checks values of the plurality of stimulation parameters against safety rules to limit these values within constraints of the safety rules. In one embodiment, the safety rules are heuristic rules.

User interface 1910 represents an embodiment of user interface 310 and allows the user to define and/or adjust the pattern of neurostimulation pulses and perform various other monitoring and programming tasks. In one embodiment, user interface 1910 includes a GUI. User interface 1910 includes display screen 642, user input device 644, and an interface control circuit 1940. Display screen 642 may include any type of interactive or non-interactive screens, and user input device 644 may include any type of user input devices that supports the various functions discussed in this document, such as touchscreen, keyboard, keypad, touchpad, trackball, joystick, and mouse. In one embodiment, user interface 1910 includes a GUI that has an interactive screen for displaying a graphical representation of a waveform building block and allows the user to adjust the waveform building block by graphically editing the waveform building block. User interface 1910 may also allow the user to perform any other functions discussed in this document where graphical editing is suitable as may be appreciated by those skilled in the art.

Interface control circuit 1940 controls the operation of user interface 1910 including responding to various inputs received by user input device 644 and defining the one or more stimulation waveforms. Interface control circuit 640 includes a stimulation adjustor 1982. Stimulation adjustor 1982 allows the user to adjust the pattern of neurostimulation pulses before programming a stimulation device such as stimulation device 104 or implantable stimulator 404 for delivery to the patent, as further discussed below with reference to FIGS. 31-38.

Remote storage device 1981 of remote device 1972 stores a plurality of waveform building blocks each selectable for use as a portion of the pattern of the neurostimulation pulses. In various embodiments, each waveform building block of the plurality of waveform building blocks includes one or more pulses of the neurostimulation pulses, and may include one or more other waveform building blocks of the plurality of waveform building blocks. Examples of such waveforms include pulses, bursts each including a group of the pulses, trains each including a group of the bursts, and sequences each including a group of the pulses, bursts, and trains.

Remote storage device 1981 also stores a plurality of stimulation fields. Each waveform building block of the plurality of waveform building blocks is associated with one or more fields of the plurality of stimulation fields. Each field of the plurality of stimulation fields is defined by one or more electrodes of the plurality of electrodes through which a pulse of the neurostimulation pulses is delivered and a current distribution of the pulse over the one or more electrodes. In various embodiments, external storage device 618 and remote storage device 1981 may store similar and/or identical types of information associated with waveform building blocks when, for example, remote device 1972 is used to compose waveform building blocks, and external programming device 1970 is used to imported the composed waveform building blocks from remote device 1972, adjust them when necessary, and apply them in programming the stimulation device such as implantable stimulator 404.

User interface 1974 of remote device 1972 allows the user to modify the waveform building blocks in remote storage device 1981 and create new waveform building blocks to store in remote storage device 1981. In one embodiment, user interface 1974 includes a GUI. User interface 1974 includes a display screen 1976, a user input device 1978, and an interface control circuit 1980. Display screen 1976 may include any type of interactive or non-interactive screens, and user input device 1978 may include any type of user input devices that supports the various functions discussed in this document, such as touchscreen, keyboard, keypad, touchpad, trackball, joystick, and mouse. In one embodiment, user interface 1974 includes a GUI that has an interactive screen for displaying a graphical representation of a waveform building block and allows the user to adjust the waveform building block by graphically editing the waveform building block. User interface 1974 may also allow the user to perform any other functions discussed in this document where graphical editing is suitable as may be appreciated by those skilled in the art.

Interface control circuit 1980 controls the operation of user interface 1974 including responding to various inputs received by user input device 1978 and defining the one or more stimulation waveforms. Interface control circuit 1920 includes a waveform composer 1920. Waveform composer 1920 represents an embodiment of waveform composer 720 and allows for composition of waveform building blocks and composition of the pattern of the neurostimulation pulses using one of more waveform building blocks, as further discussed below with reference to FIGS. 20-30.

Figure 20:
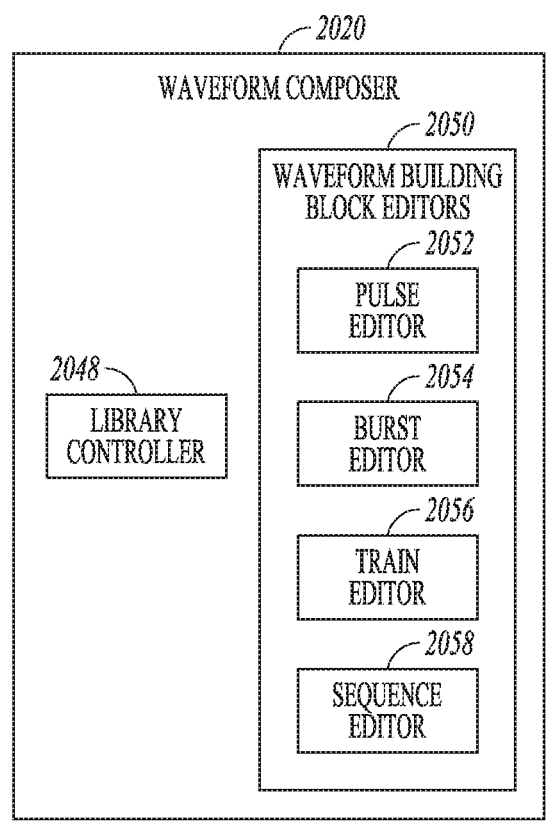
FIG. 20 illustrates an embodiment of a waveform composer of a remote device, such as the remote device of FIG. 19.

FIG. 20 illustrates an embodiment of a waveform composer 2020 of a remote device, such as remote device 1972. Waveform composer 2020 includes a library controller 2048 and a plurality of waveform building block editors 2050. In various embodiments, waveform composer 2020 is designed for use by sophisticated users such as research scientists who are biomedical engineering professionals with a deep understanding of neuromodulation and electrical engineering. They understand the science behind stimulation waveforms and the science behind coordinated reset (which is a stimulation paradigm that involves varying pulse characteristics in both the temporal and spatial domain in an effort to promote neural circuit reorganization). In various embodiments, waveform composer 2020 can be configured to perform the functions of waveform composer 820 as discussed above with reference to FIGS. 8-17 and/or the functions as discussed below with reference to FIGS. 20-30.

Library controller 2048 represents an embodiment of library controller 848 and displays a library management area on display screen 1976 in response to a user selection for access to the library controller. In various embodiments; library controller 2048 can be configured to perform the functions of library controller 848 and/or the functions discussed below with reference to FIG. 21.

FIG. 21 illustrates an embodiment of a screen (such as display screen 1976) displaying such a library management area. The library management area provides an overview and allows for selection of waveform building blocks, such as pulses, bursts, trains, and sequences, created using waveform composer 2020 and stored in remote storage device 1981. The waveform building blocks are each displayed with a type (kind), a title (name), a preview, a pulse frequency, a pulse width; a strategy (neurostimulation strategy such as subperception; coordinated reset; etc.), a source (creator of the building block), a date edited, and an action menu and are each selectable for editing by a corresponding editor of the plurality of waveform building block editors 2050. In the illustrated embodiment, a main "Library" menu includes list of waveform building blocks displayed for editing or deletion. The list may include all the waveform building blocks available from remote storage device 1981, or selected based on user-definable filtering criteria. Titles can be edited or deleted, and actions can be taken about each waveform building block. Clicking on an "i" opens an information summary about a waveform building block without having to open the waveform building block itself. Clicking the action menu icon opens a list of actions such as "Open, Duplicate, Delete, Export, Show in Menu, and I-fide in Menu".

Waveform building block editors 2050 represents an embodiment of waveform building block editors 850, and includes an editor for each type of the plurality of types of waveform building blocks. In the illustrated embodiment, waveform building block editors 2050 include a pulse editor 2052, a burst editor 2054, a train editor 2056, and a sequence editor 2058. In various embodiments, waveform building block editors 2050 can be configured to perform the functions of waveform building block editors 850 as discussed above and/or the functions discussed below with reference to FIGS. 22-30. Specifically, pulse editor 2052 can be configured to perform the functions of pulse editor 852 as discussed above and/or the functions discussed below with reference to FIGS. 22 and 23, burst editor 2054 can be configured to perform the functions of burst editor 854 as discussed above and/or the functions discussed below with reference to FIGS. 24 and 25, train editor 2056 can be configured to perform the functions of train editor 856 as discussed above and/or the functions discussed below with reference to FIGS. 26-28, and sequence editor 2058 can be configured to perform the functions of sequence editor 858 as discussed above and/or the functions discussed below with reference to FIGS. 29 and 30.

Pulse editor 2052 represents an embodiment of pulse editor 852 and displays a pulse library area on display screen 1976 in response to a user selection for access to the pulse editor. FIG. 22 illustrates an embodiment of the screen (such as display screen 1976) displaying such a pulse library area. The pulses are the smallest waveform building blocks and are each displayed with a type (kind), a title (name), a preview, a pulse frequency, a pulse width, a strategy, a source (creator of the building block), a date edited, and an action menu and are each selectable for editing by pulse editor 2052. In the illustrated embodiment, a main "Pulses" menu includes list of pulses displayed for editing or deletion. The list may include all pulses available from remote storage device 1981, or selected based on user-definable filtering criteria. The pulses can be filtered based on their characteristics (title, pulse width, strategy, source, date, etc.) for displaying. New pulses can be created and added to the main "Pulses" menu and remote storage device 1981. The pulses can be created, exported, copied, or deleted.

Figure 23:
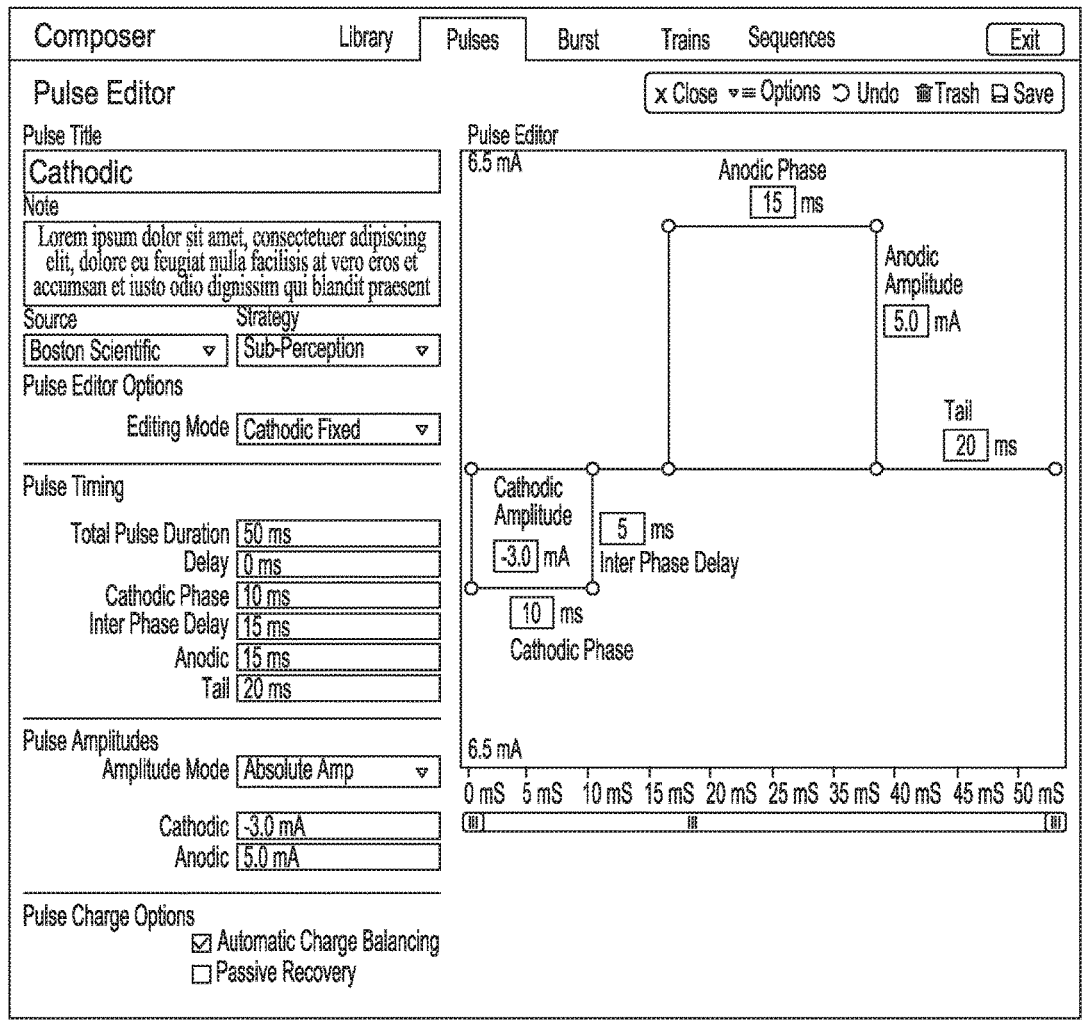
FIG. 23 illustrates an embodiment of the screen of the remote device displaying a pulse composition area.

In response to a pulse being selected, pulse editor 2052 displays a pulse composition area on display screen 1976. The pulse composition area allows the user to compose a pulse of the waveform building blocks. FIG. 23 illustrates an embodiment of the screen (such as display screen 1976) displaying such a pulse composition area. The pulse composition area allows the user to edit a pulse selected from the waveform building blocks stored in remote storage device 1981 and to create a new pulse to be added to the waveform building blocks stored in remote storage device 1981. In the illustrated embodiment, the pulse composition area allows for editing of pulse metadata. Each pulse can be given a title, a description, a source, and a strategy. A preview of the waveform of a pulse is displayed. The displayed waveform is broken down and visualized in its cathodic and anodic phase, amplitude, interphase delay, and tail. Each of these characteristics is editable graphically on the displayed waveform or by editing the parameters displayed under "Pulse Timing", "Pulse Amplitude", and "Pulse Charge Options" (automatic charge balancing or passive recovery). These parameters include the same information as observable from the displayed preview of the waveform. The Pulse Timing and Pulse Amplitude parameters define the shape of the waveform of the pulse. In one embodiment, pulse editor 2052 allows the waveform of the pulse to be edited in freeform mode, under which the waveform shape can be drawn from scratch.

Burst editor 2054 represents an embodiment of pulse editor 854 and displays a burst library area on display screen 1976 in response to a user selection for access to burst editor 2054. FIG. 24 illustrates an embodiment of the screen (such as display screen 1976) displaying such a burst library area. A burst is a sequence of pulses such as on the timescale of microseconds and seconds. Editable characteristics of a burst may include its frequency and its overall pulse width. In the illustrated embodiment, a main "Bursts" menu includes list of bursts displayed for editing or deletion. The list may include all the bursts available from remote storage device 1981, or selected based on user-definable filtering criteria. The bursts can be filtered based on their characteristics (title, pulse width, strategy, source, date, etc.) for displaying. New bursts can be created and added to the main "Bursts" menu and remote storage device 1981. The bursts can be created, exported, copied, or deleted.

Figure 25:
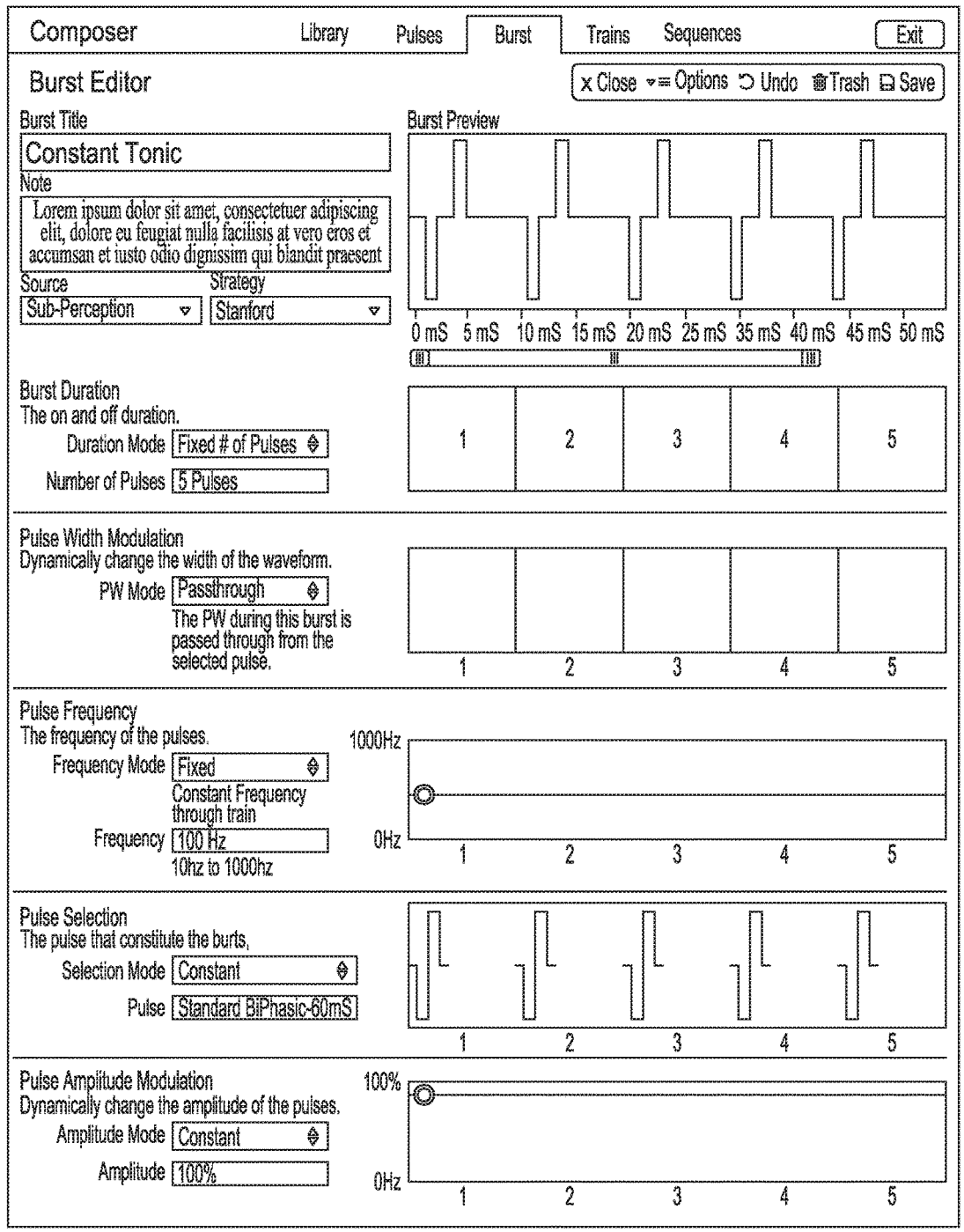
FIG. 25 illustrates an embodiment of the screen of the remote device displaying a burst composition area.

In response to a burst being selected, burst editor 2054 displays a burst composition area on display screen 1976. The burst composition area allows the user to compose a burst of the waveform building blocks. FIG. 25 illustrates an embodiment of the screen (such as display screen 1976) displaying such a burst composition area. The burst composition area allows the user to edit a burst selected from the waveform building blocks stored in remote storage device 1981 and to create a new burst to be added to the waveform building blocks stored in remote storage device 1981. In the illustrated embodiment, the burst composition area allows for editing of burst metadata. Each burst can be given a title, a description, a source, and a strategy. The shape of the burst is displayed under a "Burst Preview" area. The burst composition area allows for definition of various parameters for each burst including the burst duration (fixed, expanding, contracting, etc.) and number of pulses in the burst, the width of the pulses during the burst, the frequency of the pulses during the burst, selection of the pulses used in the burst, and the amplitude of the pulses (constant, dynamic, etc.) during the burst.

In one embodiment, which may be referred to as pulse amplitude modulation, burst editor 2054 allows the amplitude of the pulses to be edited by selecting points along the burst duration by hand and determining their percentage amplitude. In one embodiment, which may be referred to as Keyframe editing, burst editor 2054 allows the pulse width of the pulses to be edited by selecting points along the burst duration and determining their size along key points. In one embodiment, which may be referred to as score editing, burst editor 2054 allows the selection of the pulses to be edited by choosing from a set of pulses and placing them along a timeline. In one embodiment, which may be referred to as code editing, burst editor 2054 allows the selection of the pulses to be edited by writing code in a development window. The values are expressed graphically to the right of the code. In one embodiment, which may be referred to as stimulation quality nuance editing, burst editor 2054 allows additional nuanced variables can be added and edited, to add different qualities to the stimulation.

Train editor 2056 represents an embodiment of train editor 856 displays a train library area on display screen 1976 in response to a user selection for access to the train editor. FIG. 26 illustrates an embodiment of the screen (such as display screen 1976) displaying such a train library area. A train is a sequence of the pulses and bursts laid next to each other on "tracks". Whereas the pulses and bursts are comprised of changes in amplitude and duration, trains can map spatial relationships to the lead hardware. In the illustrated embodiment, a main "Trains" menu includes list of trains displayed for editing or deletion. The list may include all the trains available from remote storage device 1981, or selected based on user-definable filtering criteria. The trains can be filtered based on their characteristics (title, pulse width, strategy, source, date, etc.) for displaying. New trains can be created and added to the main "Trains" menu and remote storage device 1981. The trains can be created, exported, copied, or deleted.

Figure 27:
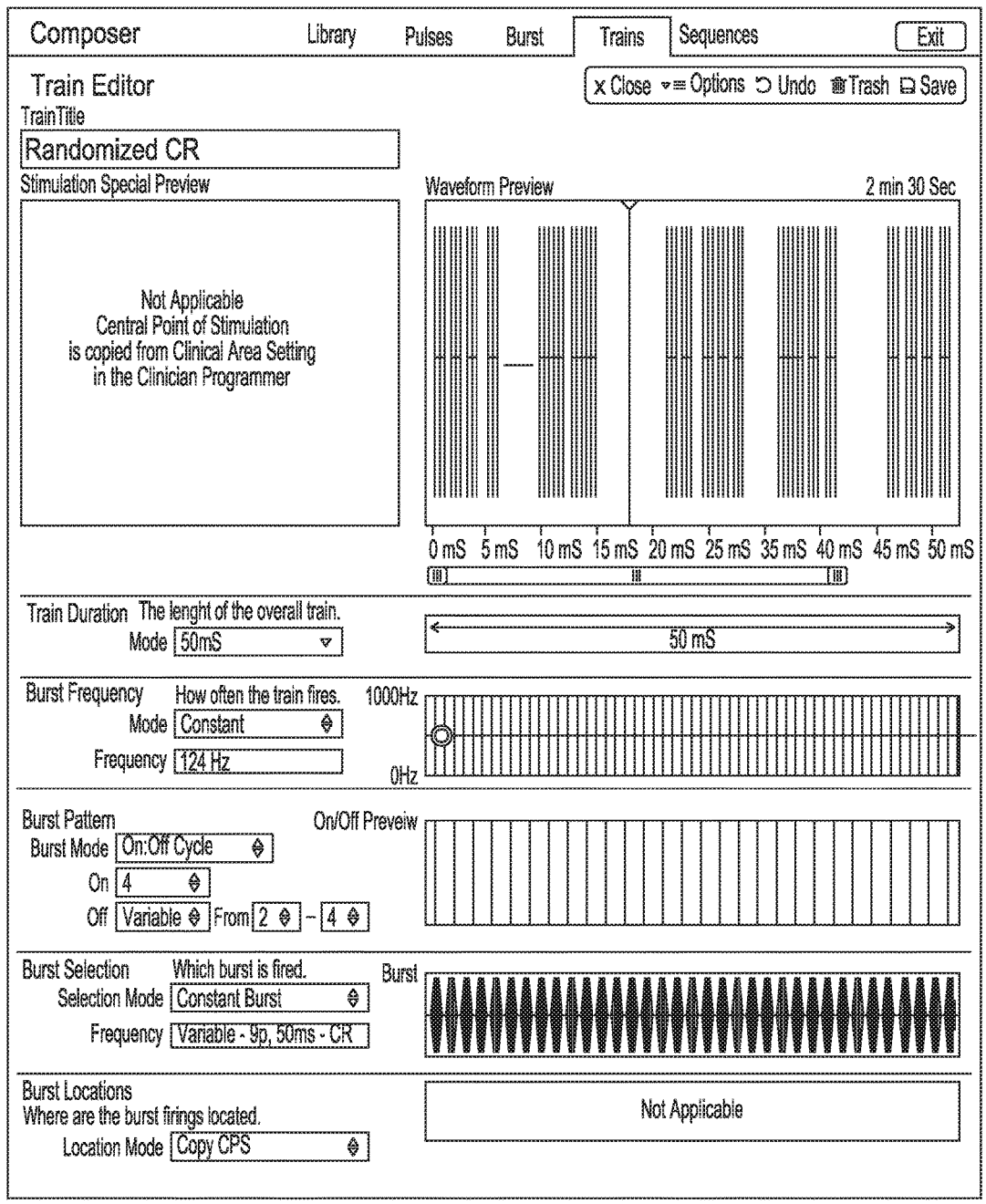
FIG. 27 illustrates an embodiment of the screen of the remote device displaying a train composition area.

In response to a train being selected, train editor 2056 displays a train composition area on display screen 1976. The train composition area allows the user to compose a train of the waveform building blocks. FIG. 27 illustrates an embodiment of the screen (such as display screen 1976) displaying such a train composition area. The train composition area allows the user to edit a train selected from the waveform building blocks stored in remote storage device 1981 and to create a new train to be added to the waveform building blocks stored in remote storage device 1981. In the illustrated embodiment, in a waveform preview area a playback head is used to scrub through the waveform of the train to review amplitude, duration, and spatial placement of the contacts, in a way similar to fast forwarding through a video clip. In a "Burst Pattern" area, patterns of bursts are either selected using a pull down numerical menus or by clicking representative on/off black/white keys in the waveform preview area. CPS parameters can be ascribed in the train composition area or left to be determined for the patient during the clinical visit.

Figure 28:
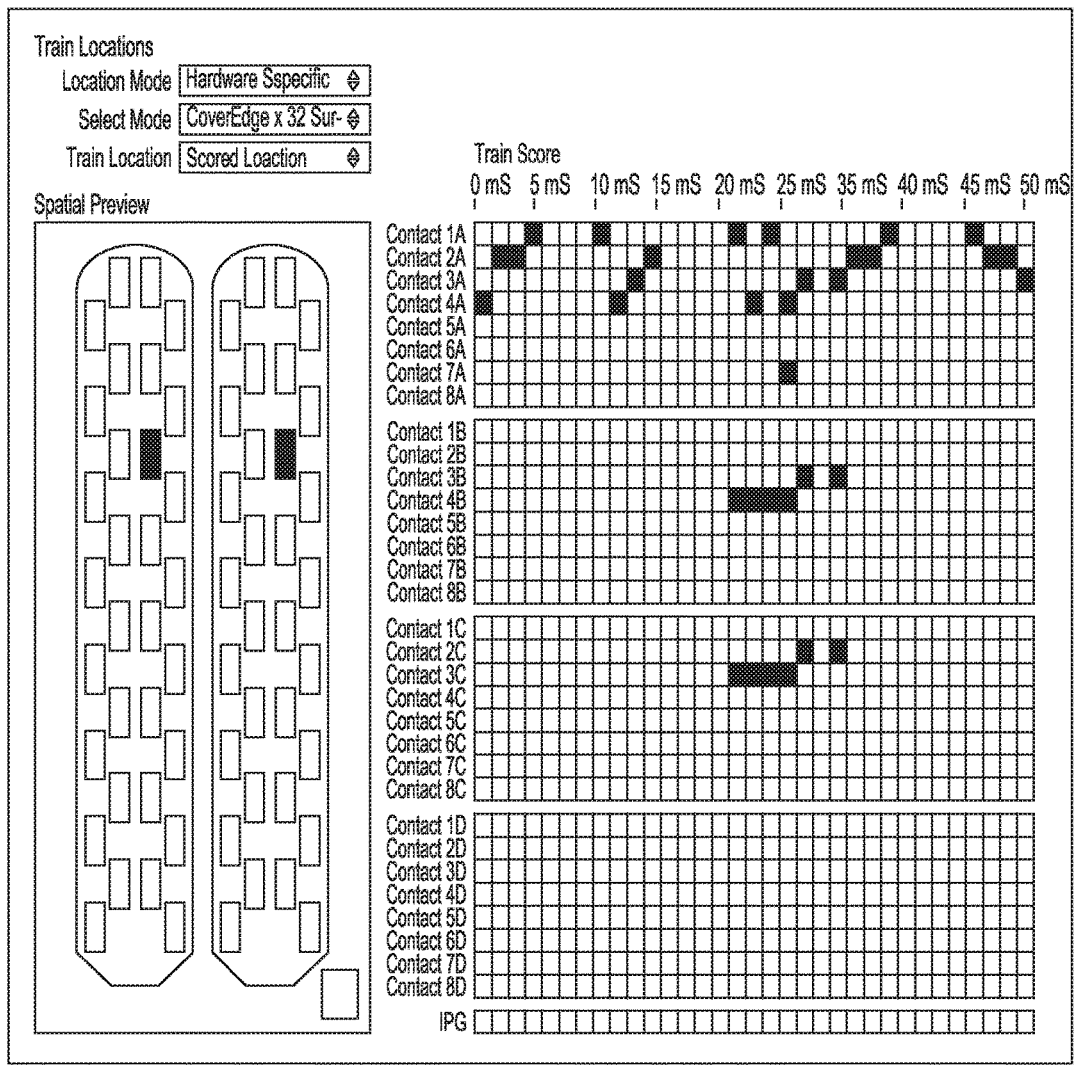
FIG. 28 illustrates an embodiment of the screen of the remote device displaying a train location area of the train composition area.

FIG. 28 illustrates an embodiment of the screen (such as display screen 1976) displaying a train location area of the train composition area. Methods for managing train location may be hardware specific. Lead information is imported into waveform composer 2020 and contact stimulation locations (electrodes) are hand selected and mapped to a temporal score. The score is aligned with the waveform preview area to enable tracking the time and location of the stimulation. Locations on the lead are assigned to Keyframes on the stimulation timeline. During the playback of the waveform, contacts (electrodes) are activated along the lead.

Sequence editor 2048 displays a sequence library area on display screen 1976 in response to a user selection for access to the sequence editor. FIG. 29 illustrates an embodiment of the screen such as display screen 1976) displaying such a sequence library area. A sequence is a combination of the pulses, burst(s), and train(s) and can be composed for application in specific therapies. In the illustrated embodiment, a main "Sequences" menu includes list of sequences displayed for editing or deletion. The list may include all the sequences available from remote storage device 1981, or selected based on user-definable filtering criteria. The sequences can be filtered based on their characteristics (title, pulse width, strategy, source, date, etc.) for displaying. New sequences can be created and added to the main "Sequences" menu and remote storage device 1981. The sequences can be created, exported, copied, or deleted.

Figure 30:
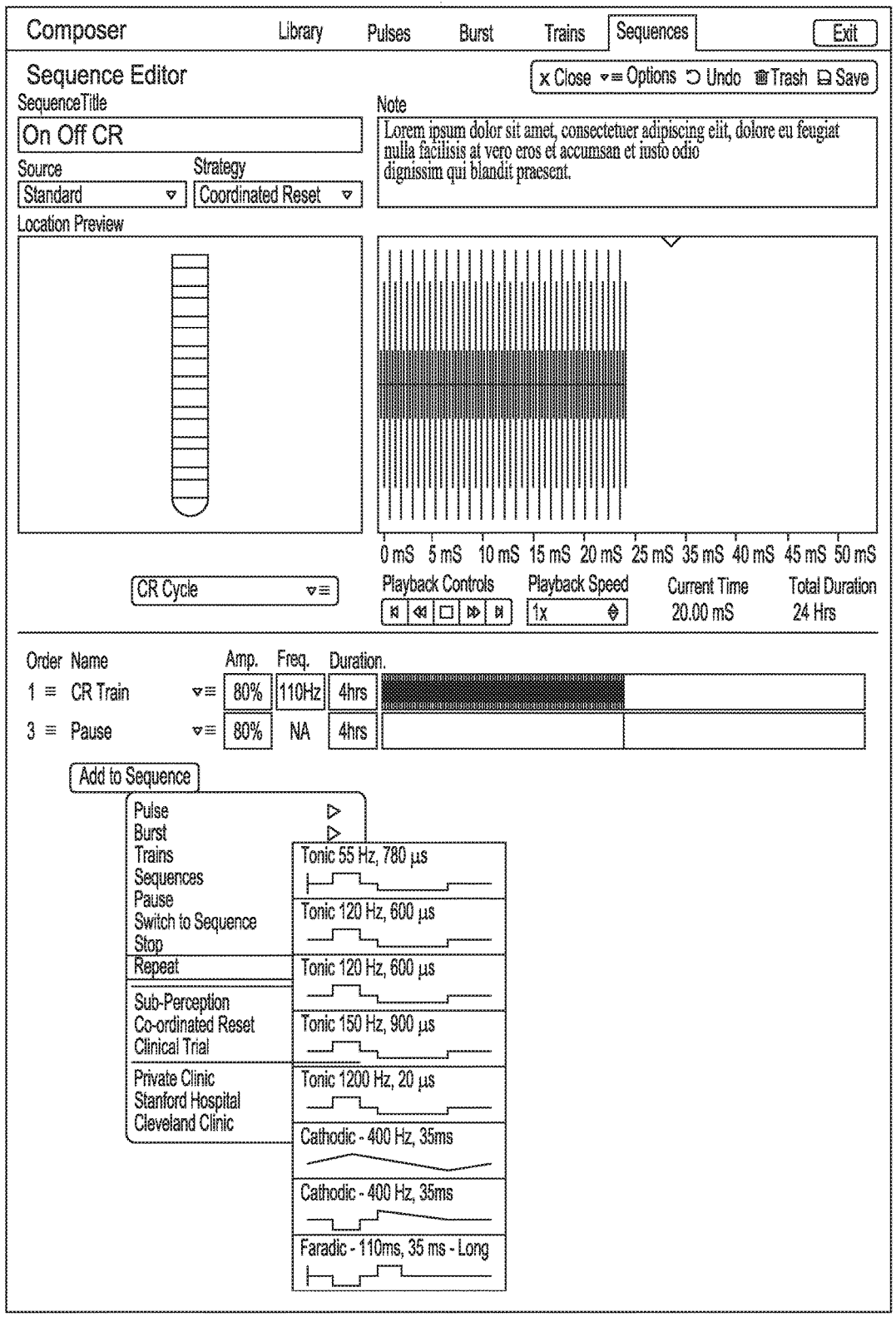
FIG. 30 illustrates an embodiment of the screen of the remote device displaying a sequence composition area.

In response to a sequence being selected, sequence editor 2058 displays a sequence composition area on display screen 1976. The sequence composition area allows the user to compose a sequence of the waveform building blocks. FIG. 30 illustrates an embodiment of the screen (such as display screen 1976) displaying such a sequence composition area. The sequence composition area allows the user to edit a sequence selected from the waveform building blocks stored in remote storage device 1981 and to create a new sequence to be added to the waveform building blocks stored in remote storage device 1981. In the illustrated embodiment, components of a sequence are displayed. Priority of the components is determined by their order in the vertical timeline. The three vertical lines represent a "holder" that reorders components. An "Add to Sequence" button enables adding components to the sequence. A pull-down menu under the "Add to Sequence" button offers components including pulse, bursts, trains, sequences, stop, repeat, etc. The sequence composition area displays the stimulation location as it plays stimulation settings. Playback controls enable scrubbing through the waveform of the sequence for review. A lead (shown as a DBS lead) is displayed in the "Location Preview" area. The user can adjust what coordinated reset (CR) program happens, for how long, and at what intensity over the course of days and weeks. For a sequence where the location of the central point of stimulation is set in a clinician programmer such as external programming device 1970), the Location Preview is not necessary.

Figure 31:
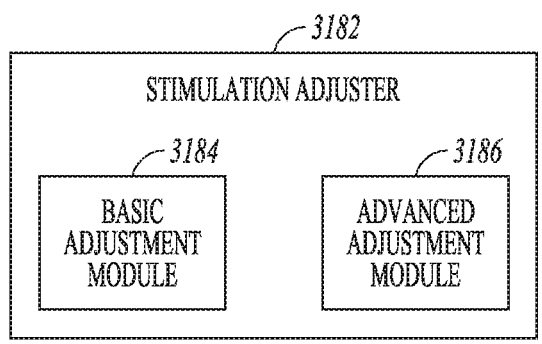
FIG. 31 illustrates an example of a stimulation adjuster of an external programming device, such as the external programming device of FIG. 19.

FIG. 31 illustrates an example of a stimulation adjuster 3182 of an external programming device, such as external programming device 1970. Stimulation adjuster 3182 represents an embodiment of stimulation adjuster 1982 and allows for adjustment of the pattern of neurostimulation pulses, such as a pattern of neurostimulation pulses composed using waveform composer 2020, before programming a stimulation device such as stimulation device 104 or implantable stimulator 404 for delivery to the patent. In the illustrated embodiment, stimulation adjuster 3182 includes a basic adjustment module 3184 and an advanced adjustment module 3186. Basic adjustment module 3184 is designed to allow users with basic skills in programming neurostimulation for their patients using user interface 1910. Examples of such users include technicians, such as nurses and sales associates, who have limited time with their patients. They spend that limited time adjusting existing parameters and ensuring a basic level of clinical efficacy. If they have time to experiment with new settings based on research, they would use a preset easily accessible in a top level menu. Advanced adjustment module 3186 is designed to allow users with advanced skills in programming neurostimulation for their patients using user interface 1910. Examples of such users include advanced clinicians, such as neurologists and researchers, who spend substantial time with their patients in a research laboratory. They understand the science behind neurostimulation and are capable of experimenting with novel settings that may affect clinical efficacy. They research and import new stimulation paradigms for use on edge case patients.

Figure 32:
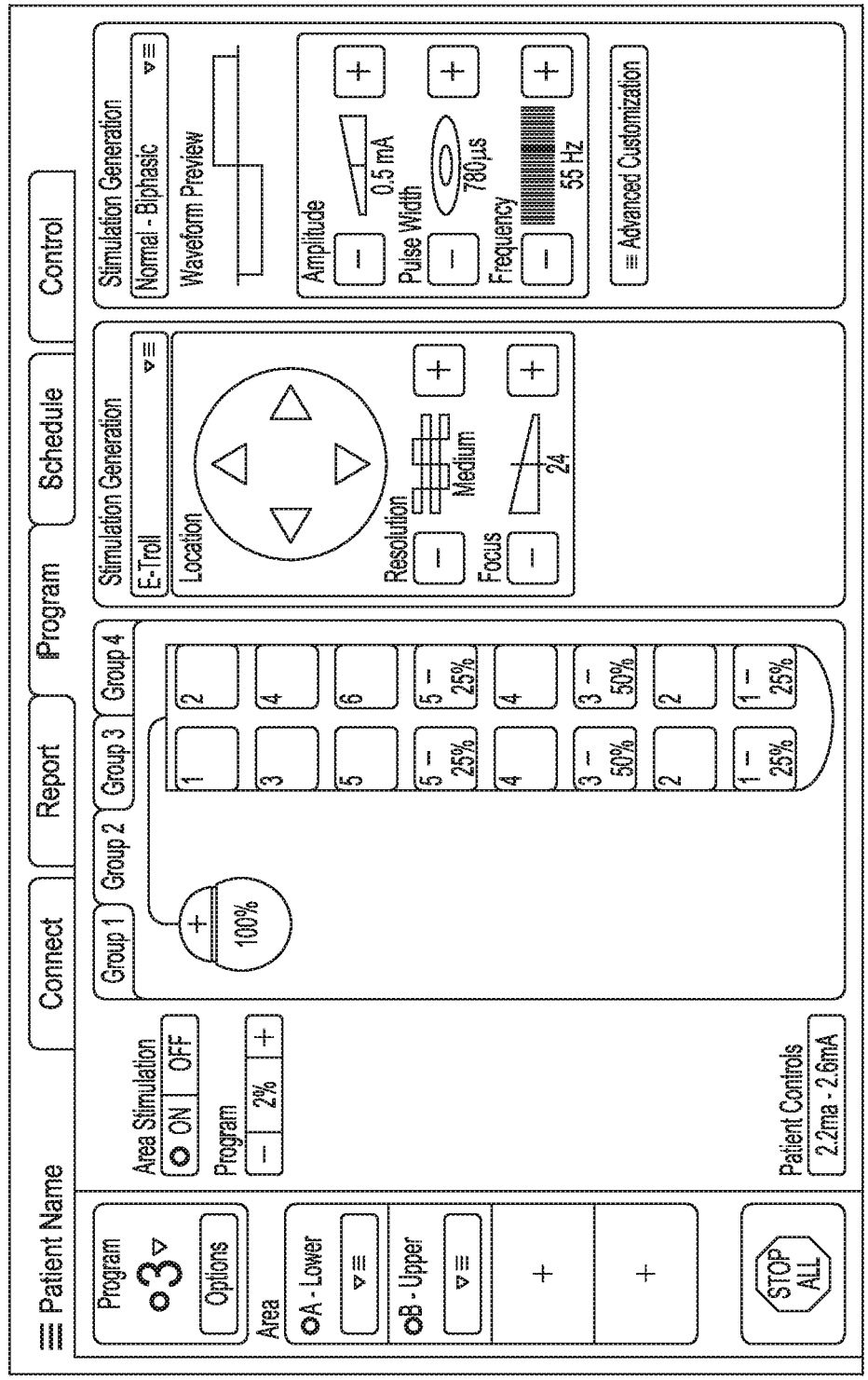
FIG. 32 illustrates an embodiment of a screen of a user interface of an external programming device, such as the external programming device of FIG. 19, with a basic adjustment area displayed.

Basic adjustment module 3184 displays a basic adjustment area on display screen 642 in response to a user selection for performing basic programming. FIG. 32 illustrates an embodiment of a screen of a user interface of an external programming device, such as display screen 642 of external programming device 1970, with a default basic adjustment area displayed. In the illustrated embodiment, the basic adjustment area includes a "Waveform Preview" area that displays iconic representation of the shape of a waveform building block (such as a biphasic phase as an example shown in FIG. 32). A "Stimulation Settings" area allows basic parameters defining the waveform building block (such as imported from remote device 1972) to be adjusted within the predefined ranges that are not editable in this area. The basic adjustment area also includes an "Advanced Settings" menu that allows for access to creating and editing the waveform building block.

In various embodiments, stimulation adjuster 3182 can be configured for specific therapy applications, with the basic adjustment module 3184 displaying a unique basic adjustment area that is suitable for each specific therapy application. Examples of such specific therapy applications include SCS, DBS, PNS, and VNS therapies.

Figure 33:
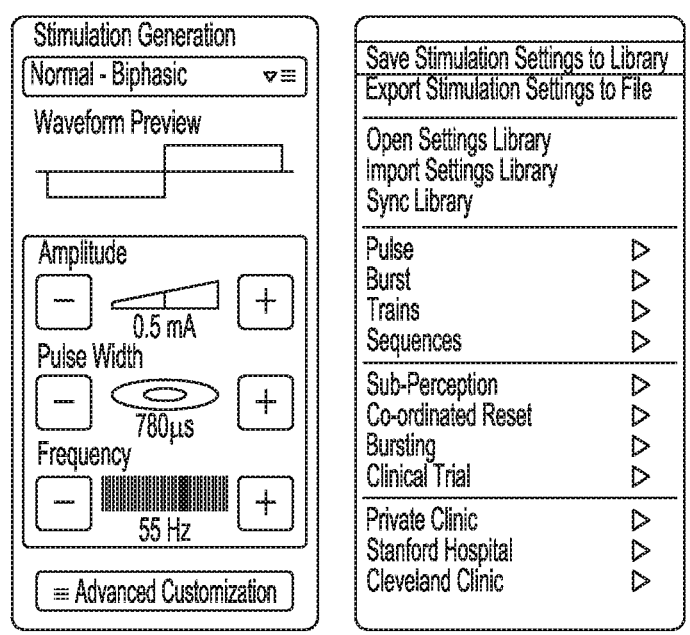
FIG. 33 illustrates an embodiment of the screen of the external programming device displaying menu options of the basic adjustment area.

FIG. 33 illustrates an embodiment of the screen (such as display screen 642) displaying menu options of the basic adjustment area. A pull-down menu allows for access to various functionality such as "Save Stimulation Settings to Library", "Export Stimulation Settings to File", "Open Settings Library", "Import Settings Library", and "Sync Library", where the Library includes various waveform building blocks stored in external storage device 618. The pull-down menu provides for submenu access to import of individual waveform building blocks including pulses, bursts, trains, and sequences, submenu access to import of specialized program sequences such as Sub-Perception, Co-ordinated Reset, and Bursting, and submenu access to import of programs (e.g., sequences) created by clinical centers of excellence or notable clinicians (sometimes referred to as "celebrity sequences"). A "Waveform Preview" area displays a sample preview that allows the user to see iconic representation of the shape of a waveform building block as well as the basic parameters defining that waveform building block. In various embodiments, waveform building blocks with special settings saved by advanced adjustment module 3186 are saved with identifiers such as a setting name, a group name, and/or a descriptive note, and are readily accessible to the user using basic adjustment module 3184. In various embodiments, waveform building blocks with settings edited using advanced adjustment module 3186 can each be displayed with a preview showing the basic parameters defining the waveform building block and a note.

Figure 34:
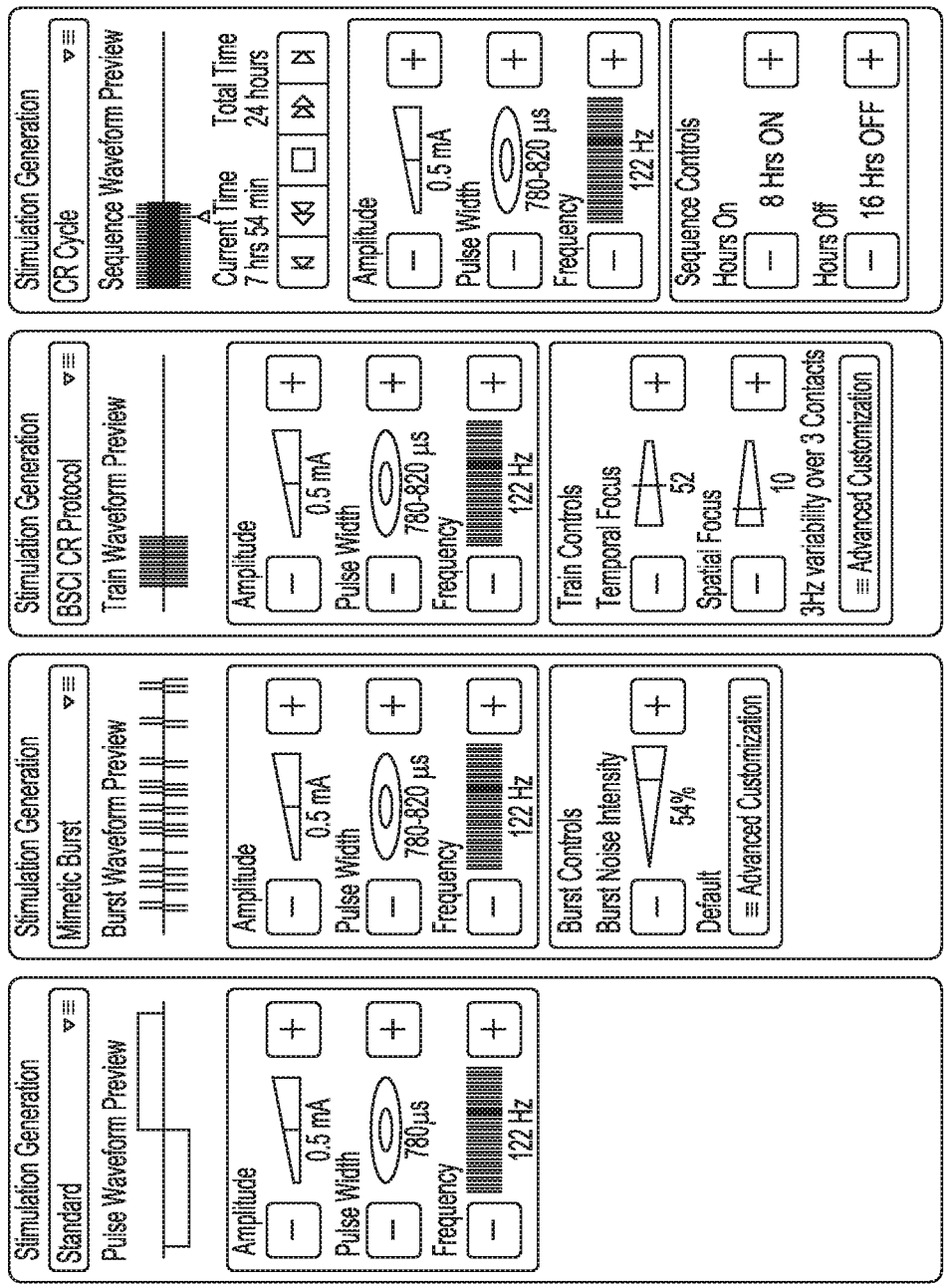
FIG. 34 illustrates an embodiment of the screen of the external programming device displaying an advanced adjustment area.

Advanced adjustment module 3186 displays an advanced adjustment area on display screen 642 in response to a user selection for performing advanced programming. FIG. 34 illustrates an embodiment of the screen (such as display screen 642) displaying a default advanced adjustment area. In the illustrated embodiment, context appropriate controls are displayed. The context of how advanced adjustment module 3186 is used determines which editing areas are displayed and operational. For example, only pulse controls are available when a pulse is being edited only burst controls are available when a burst is being edited, only train controls are available when a train is being edited, and only sequence controls are available when a sequence is being edited. Examples of such pulse, burst, train, and sequence controls are discussed below with reference to FIGS. 35-38.

Figure 35:
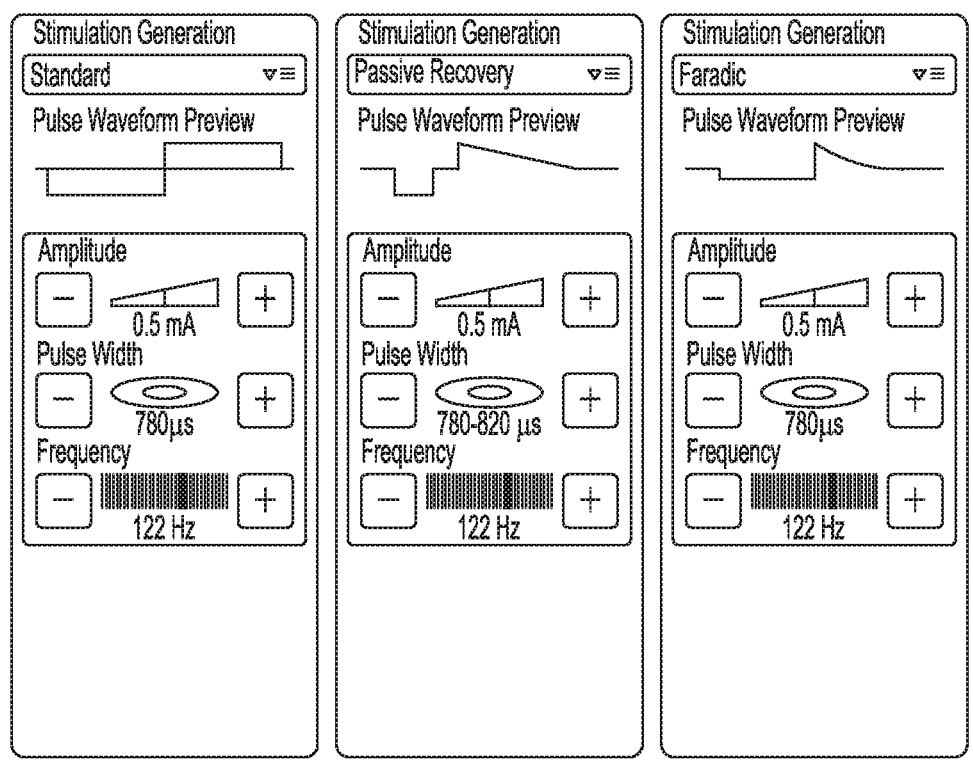
FIG. 35 illustrates an embodiment of the screen of the external programming device displaying pulse controls in the advanced adjustment area.

FIG. 35 illustrates an embodiment of the screen such as display screen 642) displaying pulse controls in the advanced adjustment area. "Pulse Waveform Preview" areas each provide quick insight into the amplitude, pulse width, and frequency of the waveform of a pulse. The basic parameters (amplitude, pulse width, and frequency as illustrated in FIG. 35) are adjustable. The values or value ranges for these basic parameters may be locked by the author of the pulse and not editable by the user of external programming device 1970.

Figure 36:
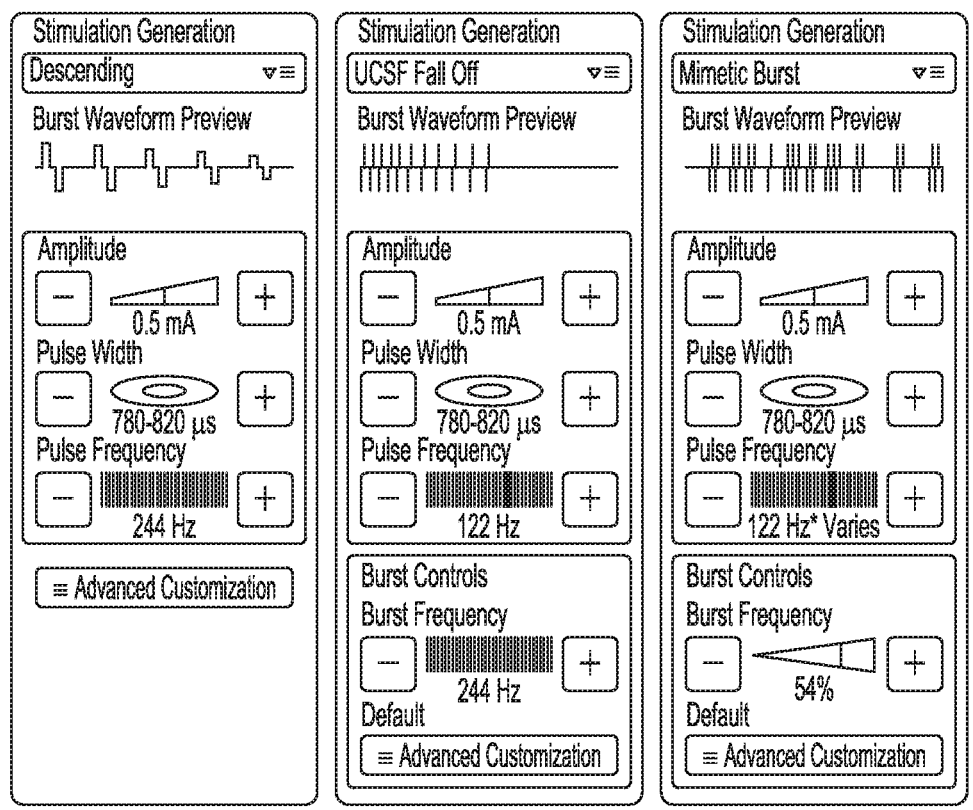
FIG. 36 illustrates an embodiment of the screen of the external programming device displaying burst controls in the advanced adjustment area.

FIG. 36 illustrates an embodiment of the screen such as display screen 642) displaying burst controls in the advanced adjustment area. "Burst Waveform Preview" areas each provide quick insight into the amplitude, pulse width, and frequency of a burst. The basic parameters (amplitude, pulse width, and frequency as illustrated in FIG. 36) are adjustable. The values or value ranges for these basic parameters may be locked by the author of the burst and not editable by the user of external programming device 1970. Only the parameter settings specific to the type of the waveform building block (e.g., burst frequency for a burst as illustrated in FIG. 36) are displayed for that type of the waveform building block. In various embodiments, advanced adjustment module 3186 may provide different means for editing the waveform depending on the parameter being adjusted, such as via linear points or graphical editing.

Figure 37:
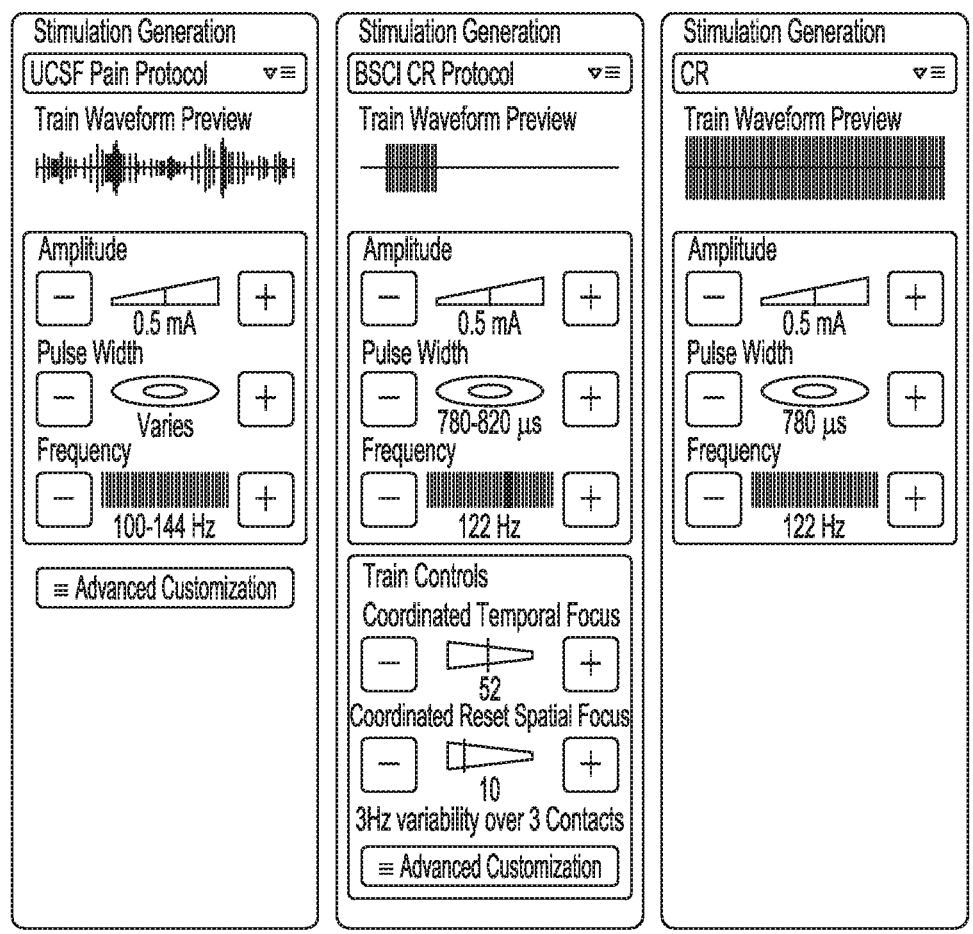
FIG. 37 illustrates an embodiment of the screen of the external programming device displaying train controls in the advanced adjustment area.

FIG. 37 illustrates an embodiment of the screen (such as display screen 642) displaying train controls in the advanced adjustment area. "Train Stimulation Preview" areas each provide quick insight into the amplitude, pulse width, and frequency of a train. The basic parameters (amplitude, pulse width, and frequency as illustrated in FIG. 36) are adjustable. The values or value ranges for these basic parameters may be locked by the author of the burst and not editable by the user of external programming device 1970. Only the parameter settings specific to the type of the waveform building block (e.g., coordinated reset temporal focus and coordinated reset spatial focus for a train as illustrated in FIG. 37) are displayed for that type of the waveform building block. In various embodiments, the train controls allow for editing across multiple contacts (electrodes).

Figure 38:
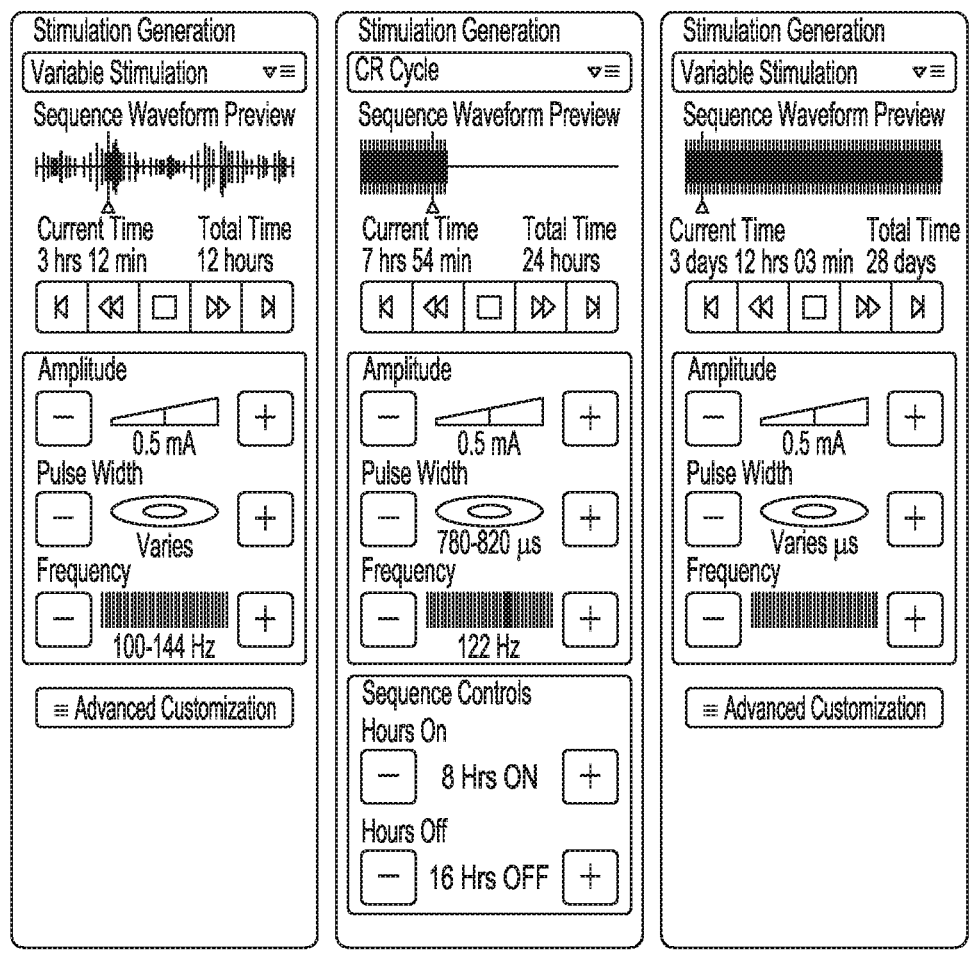
FIG. 38 illustrates an embodiment of the screen of the external programming device displaying sequence controls in the advanced adjustment area.

FIG. 38 illustrates an embodiment of the screen such as display screen 642) displaying sequence controls in the advanced adjustment area. "Sequence Stimulation Preview" areas each provide quick insight into the time and duration of an entire sequence while allowing a playback head to move back and forth along the timeline of the sequence. The values or value ranges for basic parameters of the sequence may be locked by the author of the burst and not editable by the user of external programming device 1970. Parameter controls specific to sequence and coordinate reset are displayed only when appropriate. An "Advanced Customization" menu enables, among other things, editing of on/off times for the sequence. In various embodiments, the sequence controls allow for control options such as "Varies (allowing pulse width, pulse, amplitude, and/or pulse frequency to vary through the duration of the sequence), Random (allowing a component of a sequence to have a degree of randomness, such as random pulse width within a range, random pulse frequency within a range, and/or random electrode configuration within a given spatial location), and Noise (allowing noise to be added to a stimulation parameter for possible positive clinical effect)" to enable limited and/or unlimited variability in the sequence.

In various embodiments, system 100 may include any one or any combination of the physical and functional structures discussed above and/or one or more other physical and functional structures configured to be used in programming a stimulation device for neurostimulation. In addition to the Examples 1-22 discussed in the Summary Section above, some other non-limiting examples are provided as follows.

An example (e.g., "Example 23") of a system for a user to program a neurostimulator configured to deliver neurostimulation to a patient may include a storage device, a programming control circuit, and a user interface. The storage device may be configured to store waveform building blocks. The programming control circuit may be configured to generate a plurality of stimulation parameters controlling delivery of neurostimulation pulses from the neurostimulator according to a pattern of the neurostimulation pulses. The user interface may include a display screen, a user input device, and an interface control circuit coupled to the display screen and the user input device. The interface control circuit may include a waveform composer that may be configured to allow for composition of one of more building blocks of the waveform building blocks and composition of the pattern of the neurostimulation pulses using one of more building blocks selected from the waveform building blocks. The waveform composer may include a library controller and a plurality of waveform building block editors. The library controller may be configured to display a library management area on the screen. The displayed library management area allows the user to manage the waveform building blocks stored in the storage device. The plurality of waveform building block editors may each be configured to display a composition area for a type of the waveform building blocks of a plurality of types of the waveform building blocks on the screen. The displayed composition area allows the user to compose a building block of the type of the waveform building blocks.

In Example 24, the subject matter of Example 23 may optionally be configured such that the user interface includes a graphical user interface (GUI).

In Example 25, the subject matter of any one or any combination of Examples 23 and 24 may optionally be configured such that each editor of the plurality of waveform building block editors is configured to display the composition area to allow the user to edit a building block selected from the waveform building blocks stored in the storage device.

In Example 26, the subject matter of Example 25 may optionally be configured such that each editor of the plurality of waveform building block editors is further configured to display the composition area to allow the user to create a new building block to be added to the waveform building blocks stored in the storage device.

In Example 27, the subject matter of any one or any combination of Examples 2.3 to 26 may optionally be configured such that the waveform composer is configured to allow the delivery of the neurostimulation pulses to be turned on and off by the user during the composition of waveform building blocks and composition of the pattern of the neurostimulation pulses.

In Example 28, the subject matter of any one or any combination of Examples 23 to 27 may optionally be configured such that the waveform composer is configured to allow one of the library controller and editors of the plurality of waveform building block editors to be selected by the user for access one at a time.

In Example 29, the subject matter of Example 28 may optionally be configured such that the library controller is configured to display the library management area on the screen in response to a user selection for access to the library controller, and the library management area displays the waveform building blocks each selectable for editing by a corresponding editor of the plurality of waveform building block editors.

In Example 30, the subject matter of Example 29 may optionally be configured such that the library controller is further configured to allow for importation of a new waveform building block to be added to the waveform building blocks in the storage device.

In Example 31, the subject matter of Example 30 may optionally be configured such that the library controller is further configured to allow for exportation of a waveform building block selected from the waveform building blocks in the storage device.

In Example 32, the subject matter of any one or any combination of Examples 28 to 31 may optionally be configured such that the plurality of waveform building block editors comprises a pulse editor configured to display a pulse composition area on the screen in response to a user selection for access to the pulse editor. The pulse composition area allows the user to compose a pulse of the waveform building blocks.

In Example 33, the subject matter of Example 32 may optionally be configured such that the plurality of waveform building block editors comprises a burst editor configured to display a burst composition area on the screen in response to a user selection for access to the burst editor. The burst composition area allows the user to compose a burst of the waveform building blocks, the burst including a group of the pulses.

In Example 34, the subject matter of Example 33 may optionally be configured such that the plurality of waveform building block editors comprises a train editor configured to display a train composition area on the screen in response to a user selection for access to the train editor. The train composition area allows the user to compose a train of the waveform building blocks, the train including a group of the bursts.

In Example 35, the subject matter of Example 34 may optionally be configured such that the plurality of waveform building block editors comprises a sequence editor configured to display a sequence composition area on the screen in response to a user selection for access to the sequence editor. The sequence composition area allows the user to compose a sequence of the waveform building blocks, the sequence including a group of the pulses, bursts, and trains.

In Example 36, the subject matter of any one or any combination of Examples 23 to 35 may optionally be configured such that the waveform composer further comprises a controls editor configured to display a controls area on the screen in response to a user command. The controls area allows the user to edit pulse parameters for a waveform building block selected from the waveform building blocks.

In Example 37, the subject matter of any one or any combination of Examples 23 to 36 may optionally be configured such that the pulse parameters for the selected waveform building block comprise at least a pulse amplitude and a pulse type for each pulse in the selected waveform building block.

An example (e.g., "Example 38") of a method for operating a programming device for neurostimulation is also provided. The method may include storing waveform building blocks in a storage device of the programming device, allowing a user to perform waveform composition using a user interface of the programming device, and generating a plurality of stimulation parameters controlling delivery of neurostimulation pulses from the neurostimulator according to a pattern of the neurostimulation pulses. The waveform composition may include composition of one of more building blocks of the waveform building blocks and composition of a pattern of the neurostimulation pulses using one of more building blocks selected from the waveform building blocks. To allow the user to perform the waveform composition, a library management area may be displayed on a screen of the user interface, and a composition area for a type of the waveform building blocks of a plurality of types of the waveform building blocks may be displayed on the screen. The displayed library management area allows the user to manage the stored waveform building blocks using a user input device of the user interface. The displayed composition area allows the user to compose a building block of the type of the waveform building blocks using the user input device.

In Example 39, the subject matter of displaying the composition area as found in Example 38 may optionally include displaying the composition area to allow the user to edit a building block selected from the stored waveform building blocks and to allow the user to create a new building block to be added to the stored waveform building blocks.

In Example 40, the subject matter of Example 39 may optionally further include allowing the user to import a building block to be added to the stored waveform building blocks and to export a building block selected from the stored waveform building blocks.

In Example 41, the subject matter of allowing the user to perform waveform composition as found in claim 40 may optionally include receiving a user selection and displaying the library management area or the composition area, one at a time, according to the user selection, and the composition area corresponds to the type of the waveform building blocks selected from the plurality of types of the waveform building blocks according to the user selection.

In Example 42, the subject matter of displaying the library management area as found in Example 41 may optionally include displaying the waveform building blocks each selectable for editing.

In Example 43, the subject matter of the plurality of types of the waveform building blocks as found in Example 41 may optionally include pulses, bursts each including a group of the pulses, trains each including a group of the bursts, and sequences each including a group of the pulses, the bursts, and the trains.

In Example 44, the subject matter of allowing the user to perform waveform composition as found in Example 41 may optionally further include displaying a controls area on the screen in response to a user command The controls area allows the user to edit pulse parameters for a waveform building block selected from the waveform building blocks.

It is to be understood that the above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A system for use by a user to program a neurostimulator configured to deliver neurostimulation to a patient, comprising:
    a first storage device configured to store waveform building blocks; and
    a first user interface including a first display screen, a first user input device, and a first interface control circuit coupled to the first display screen and the first user input device, the first interface control circuit including a waveform composer configured to allow for composition of one of more building blocks of the waveform building blocks and composition of a pattern of neurostimulation pulses using one of more building blocks selected from the waveform building blocks, the waveform composer including:
        a library controller configured to display a library management area on the first display screen, the displayed library management area allowing the user to manage the waveform building blocks stored in the storage device; and
        a plurality of waveform building block editors each configured to allow the user to compose a type of the waveform building blocks of a plurality of types of the waveform building blocks, the plurality of waveform building block editors including:
            a pulse editor configured to display a pulse composition area on the first display screen in response to a user selection for access to the pulse editor, the pulse composition area allowing the user to compose a pulse of the waveform building blocks; and
            a burst editor configured to display a burst composition area on the first display screen in response to a user selection for access to the burst editor, the burst composition area allowing the user to compose a burst of the waveform building blocks, the burst including a group of pulses of the waveform building blocks.

2. The system of claim 1, further comprising a programming control circuit configured to generate a plurality of stimulation parameters controlling delivery of neurostimulation pulses from the neurostimulator according to the pattern of the neurostimulation pulses.

3. The system of claim 2, comprising:
    a remote device including the first storage device and the first user interface; and
    an external programming device including the programming control circuit.

4. The system of claim 3, wherein the external programming device is configured to import one or more of one or more waveform building blocks of the waveform building blocks or the pattern of the neurostimulation pulses from the remote device, the external programming device including a second user interface including a second display screen, a second user input device, and a second interface control circuit coupled to the second display screen and the second user input device, the second interface control circuit including a stimulation adjuster configured to allow for adjustment of the imported one or more of the one or more waveform building blocks of the waveform building blocks or the pattern of the neurostimulation pulses.

5. The system of claim 1, wherein the waveform composer is configured to allow the delivery of the neurostimulation pulses to be turned on and off by the user during the composition of the one or more building blocks of the waveform building blocks and during the composition of the pattern of the neurostimulation pulses.

6. The system of claim 1, wherein the waveform composer is configured to allow one of the library controller and editors of the plurality of waveform building block editors to be selected by the user for access one at a time, and the library controller is configured to display the library management area on the first display screen in response to a user selection for access to the library controller, and the library management area displays the waveform building blocks each selectable for editing by a corresponding editor of the plurality of waveform building block editors.

7. The system of claim 6, wherein the library controller is further configured to allow for importation of a new waveform building block to be added to the waveform building blocks in the first storage device and to allow for exportation of a waveform building block selected from the waveform building blocks in the first storage device.

8. The system of claim 7, wherein each editor of the plurality of waveform building block editors is configured to display a library area on the first display screen in response to a user request for access to that editor, the library area listing available waveform building blocks of a type of the waveform building blocks of the plurality of types of the waveform building blocks.

9. The system of claim 8, wherein the each editor is configured to display a composition area for the type of the waveform building blocks on the first display screen in response to a waveform building block being selected from the listed waveform building blocks, the composition area allowing the user to edit the selected waveform building block or to create a new building block to be added to the waveform building blocks stored in the first storage device.

10. The system of claim 1, wherein the plurality of waveform building block editors further comprises a train editor configured to display a train composition area on the first display screen in response to a user selection for access to the train editor, the train composition area allowing the user to compose a train of the waveform building blocks, the train including a group of the bursts.

11. The system of claim 10, wherein the plurality of waveform building block editors further comprises a sequence editor configured to display a sequence composition area on the first display screen in response to a user selection for access to the sequence editor, the sequence composition area allowing the user to compose a sequence of the waveform building blocks, the sequence including a group of the pulses, bursts, and trains.

12. A method for operating an external system for programming a neurostimulator, comprising:
    storing waveform building blocks in a storage device of the external system;
    allowing a user to perform waveform composition using a user interface of the external system, the waveform composition including composition of one of more building blocks of the waveform building blocks and composition of a pattern of neurostimulation pulses using one of more building blocks selected from the waveform building blocks, the allowing the user to perform the waveform composition including:

displaying a library management area on a screen of the user interface, the displayed library management area allowing the user to manage the stored waveform building blocks using a user input device of the user interface; and allowing the user to select a waveform building block from the stored waveform building blocks and edit the selected waveform building block using the user input device, including:

displaying a library area for a type of the waveform building blocks of a plurality of types of the waveform building blocks on the screen, the displayed library area allowing the user to select a building block of the type of the waveform building blocks using the user input device, the plurality of types of the waveform building blocks including pulses and bursts each including a group of the pulses; and displaying a composition area for the type of the waveform building blocks on the screen in response to the selection of the building block of the type of the waveform building blocks, the displayed composition area allowing the user to edit the selected building block of the type of the waveform building blocks using the user input device; and generating a plurality of stimulation parameters controlling delivery of neurostimulation pulses from a neurostimulator according to the pattern of the neurostimulation pulses using the external system.

13. The method of claim 12, comprising allowing the user to perform the waveform composition using a remote device of the external system, and further comprising allowing another user to adjust the composed one of more building blocks of the waveform building blocks and the composed pattern of the neurostimulation pulses using an external programming device of the external system, the external programming device communicatively coupled to the remote device.

14. The method of claim 12, wherein displaying the composition area further comprises displaying the composition area to allow the user to create a new building block to be added to the stored waveform building blocks.

15. The method of claim 12, further comprising allowing the user to create a new building block to be added to the stored waveform building blocks.

16. The method of claim 12, wherein the plurality of types of the waveform building blocks further comprises trains each including a group of the bursts.

17. The method of claim 16, wherein the plurality of types of the waveform building blocks further comprises sequences each including a group of the pulses, the bursts, and the trains.

18. The method of claim 12, further comprising allowing the user to import a building block to be added to the stored waveform building blocks.

19. The method of claim 18, further comprising allowing the user to export a building block selected from the stored waveform building blocks.

20. The method of claim 12, further comprising:
delivering the neurostimulation pulses from an implantable neurostimulator; and
controlling the delivery of the neurostimulation pulses using the plurality of stimulation parameters.

* * * * *